United States Patent
Hirao et al.

(10) Patent No.: US 8,993,255 B2
(45) Date of Patent: Mar. 31, 2015

(54) PROTEIN HAVING FRUCTOSYL VALYL HISTIDINE OXIDASE ACTIVITY, MODIFIED PROTEIN, AND USE OF THE PROTEIN OR THE MODIFIED PROTEIN

(75) Inventors: Rie Hirao, Fukui (JP); Masao Kitabayashi, Fukui (JP); Yoshiaki Nishiya, Fukui (JP); Hiroki Ishida, Kyoto (JP); Yoji Hata, Kyoto (JP)

(73) Assignees: Toyo Boseki Kabushiki Kaisha, Osaka (JP); Gekkeikan Sake Co., Ltd., Kyoto (JP)

( * ) Notice: Subject to any disclaimer, the term of this patent is extended or adjusted under 35 U.S.C. 154(b) by 452 days.

(21) Appl. No.: 13/123,052

(22) PCT Filed: Oct. 6, 2009

(86) PCT No.: PCT/JP2009/005173
§ 371 (c)(1),
(2), (4) Date: Apr. 7, 2011

(87) PCT Pub. No.: WO2010/041419
PCT Pub. Date: Apr. 15, 2010

(65) Prior Publication Data
US 2011/0195444 A1    Aug. 11, 2011

(30) Foreign Application Priority Data

Oct. 10, 2008 (JP) ................. 2008-263825
Mar. 31, 2009 (JP) ................. 2009-087172
Mar. 31, 2009 (JP) ................. 2009-087211

(51) Int. Cl.
| | | |
|---|---|---|
| C12Q 1/00 | (2006.01) | |
| C12Q 1/26 | (2006.01) | |
| C12N 11/00 | (2006.01) | |
| C12N 9/02 | (2006.01) | |
| G01N 33/72 | (2006.01) | |
| C12N 9/06 | (2006.01) | |

(52) U.S. Cl.
CPC ............ G01N 33/723 (2013.01); C12N 9/0022 (2013.01); C12Q 1/26 (2013.01)
USPC ............................. 435/25; 435/174; 435/189

(58) Field of Classification Search
None
See application file for complete search history.

(56) References Cited

U.S. PATENT DOCUMENTS

| | | | |
|---|---|---|---|
| 6,352,835 | B1 | 3/2002 | Komori et al. |
| 6,514,720 | B2 | 2/2003 | Komori et al. |
| 7,018,823 | B2 | 3/2006 | Kurosawa et al. |
| 7,235,378 | B2 | 6/2007 | Yonehara |
| 7,419,813 | B2 | 9/2008 | Kurosawa et al. |
| 7,449,305 | B2 | 11/2008 | Yonehara et al. |
| 7,588,910 | B2 | 9/2009 | Matsuoka et al. |
| 2002/0025546 | A1 | 2/2002 | Komori et al. |
| 2003/0157593 | A1 | 8/2003 | Kurosawa et al. |
| 2003/0162242 | A1 | 8/2003 | Yonehara |
| 2004/0248226 | A1 | 12/2004 | Yonehara |
| 2005/0042709 | A1 | 2/2005 | Yonehara et al. |
| 2005/0244926 | A1 | 11/2005 | Kurosawa et al. |
| 2007/0037243 | A1 | 2/2007 | Hirokawa et al. |
| 2007/0154976 | A1 | 7/2007 | Taniguchi et al. |
| 2008/0113381 | A1 | 5/2008 | Matsuoka et al. |
| 2008/0193960 | A1 | 8/2008 | Hirokawa et al. |
| 2008/0233605 | A1 | 9/2008 | Taniguchi et al. |
| 2009/0011467 | A1 | 1/2009 | Kurosawa et al. |
| 2009/0239239 | A1 | 9/2009 | Hirokawa et al. |
| 2009/0317851 | A1 | 12/2009 | Matsuoka et al. |

FOREIGN PATENT DOCUMENTS

| | | |
|---|---|---|
| EP | 1626088 | 2/2006 |
| EP | 2020439 | 2/2009 |
| EP | 2281900 | 2/2011 |
| EP | 2287295 | 2/2011 |
| EP | 2357228 | 8/2011 |
| JP | 2003-235585 | 8/2003 |
| JP | 2004-113014 | 4/2004 |
| JP | 2004-129531 | 4/2004 |
| JP | 2004-275013 | 10/2004 |
| JP | 2004-275063 | 10/2004 |
| JP | 2005-110657 | 4/2005 |
| JP | 2007-181466 | 7/2007 |
| JP | 3971702 | 9/2007 |
| JP | 2007-289202 | 11/2007 |

(Continued)

OTHER PUBLICATIONS

Birren, B. et al., NCBI Reference Sequence: XP_001798711, Hypothetical protein SNOG_08398 [*Phaeosphaeria nodorum* SN 15], Apr. 2, 2008.

Birren, B. et al., NCBI Reference Sequence: XM_001798659, *Phaeosphaeria nodorum* SN 15 hypothetical protein partial mRNA, Apr. 2, 2008.

GenBank Accession No. CH445336.1, *Phaeosphaeria nodorum* SN15 scaffold_12, whole genome shotgun sequence, Nov. 23, 2007.

Hirokawa, K., et al., Distribution and properties of novel deglycating enzymes for fructosyl peptide in fungi, Arch Microbiol (2003) 180:227-231.

(Continued)

*Primary Examiner* — Lisa J Hobbs
(74) *Attorney, Agent, or Firm* — Roylance, Abrams, Berdo & Goodman, L.L.P.

(57) ABSTRACT

The present invention provides: a protein having a fructosyl amino acid oxidase activity which protein is useful for measurement of a glycosylated protein (particularly, glycosylated hemoglobin); a modified protein thereof; and use of the protein or the modified protein. The protein of the present invention is, for example, a fructosyl valyl histidine oxidase derived from *Phaeosphaeria nodorum*, the fructosyl valyl histidine oxidase having excellent thermal stability and substrate specificity and also having a small Km value to fructosyl valyl histidine. This allows a glycosylated protein measuring reagent to be stored in a long time and measurement accuracy of the glycosylated protein measuring reagent to be improved.

7 Claims, 1 Drawing Sheet

(56) References Cited

FOREIGN PATENT DOCUMENTS

| | | |
|---|---|---|
| JP | 4010474 | 11/2007 |
| JP | 4014088 | 11/2007 |
| JP | 4039664 | 1/2008 |
| JP | 4045322 | 2/2008 |
| WO | 03-064683 | 8/2003 |
| WO | 2004-104203 | 12/2004 |
| WO | 2005-049857 | 6/2005 |
| WO | 2005-049858 | 6/2005 |
| WO | 2007-010950 | 1/2007 |
| WO | 2007-125779 | 11/2007 |

OTHER PUBLICATIONS

Hirokawa, K., et al., Molecular cloning and expression of novel fructosyl peptide oxidases and their application for the measurement of glycated protein, Biochemical and Biophysical Research Communications 311 (2003) 104-111.

Birren, B., et al., NCBI Accession: Q0UIL6 [GI: 121935412], Definition: Hypothetical protein, Nov. 28, 2006.

Hane, J., et al., Dothideomycete-Plant Interactions Illuminated by Genome Sequencing and EST Analysis of the Wheat Pathogen *Stagonospora nodorum*, The Plant Cell, vol. 19:3347-3368, Nov. 2007.

Yoshida, N., et al., Functional Analysis of Genes Encoding Putative Oxidoreductases in *Aspergillus oryzae*, Which Are Similar to Fungal Fructosyl-Amino Acid Oxidase, Journal of Bioscience and Bioengineering, vol. 104, No. 5, 424-427, 2007.

Nanjo, Y., et al., Determination of Fructosyl Amino Acids and Fructosyl Amino Acids and Fructosyl Peptides in Protease-digested Blood Sample by a Flow-Injection System with an Enzyme Reactor, Analytical Sciences, Aug. 2006, vol. 22:1139-1143.

Hirokawa, K., et al., Enhancement of thermostability of fungal deglycating enzymes by directed evolution, Appl Microbiol Biotechnol (2008) 78:775-781.

International Search Report for PCT/JP2009/005173 dated Nov. 10, 2009.

[ GENETYX-WIN : Amino Acid Sequence Homology Data ]

Date : 2009.08.25

1st Amino Acid Sequence
   File Name      : Phaeosphaeria_nodorum.ptn
   Sequence Size  : 437

2nd Amino Acid Sequence
   File Name      : Curvlaria claveta.ptn
   Sequence Size  : 441

Unit Size to Compare = 2
   Pick up Location    = 1

[85.5% / 433 aa]    INT/OPT.Score : <   1504/  1977 >

```
   1' MAPSRANTSVIVVGGGGTIGSSTALHLVRSGYTPSNVTVLDAYPIPSSQSAGNDLNKIMG
      ******************************.****.*****.*************
   1" MAPSRANTSVIVVGGGGTIGSSTALHLVRSGYTPSNITVLDTYPIPSAQSAGNDLNKIMG

61' VSLRNPVDLQLALEARQMWNEDELFKKFFHNTGRLDCAHGEKDIADLKSGYQALVD--AG
      ..*** *****.*******.**.***..*************...***. .****.*  **
  61" IRLRNKVDLQLSLEARQMWREDDLFKEYFHNTGRLDCAHGEEGLADLRQAYQALLDANAG

119' LDATNEWLDSEDEILKRMPLLSRDQIKGWKAIFSKDGGWLAAAKAINAVGEYLRDQGVRF
      *..*.**********.****.*.*******..*.*************.*********.*
 121" LEETTEWLDSEDEILKKMPLLDREQIKGWKAVYSQDGGWLAAAKAINAIGEYLRDQGVKF

179' GFYGAGSFKAPLLAEGVCIGVETVDGTRYYADKVVLAAGAWSPTLVELHEQCVSKAWVYG
      ** ******.*******************************.**.*..*********.
 181" GFGGAGSFKQPLLAEGVCIGVETVDGTRYYADKVVLAAGAWSPVLVDLEDQCVSKAWVYA

239' HIQLTPEEAARYKNSPVVYNGDVGFFFEPNEHGVIKVCDEFPGFTRFKMHQPFGAKAPKR
      ********** *** **************.******************* ***.*******
 241" HIQLTPEEAAEYKNVPVVYNGDVGFFFEPDEHGVIKVCDEFPGFTRFKQHQPYGAKAPKR

299' ISVPRSHAKHPTDTIPDASDVSIRRAIATFMPQFKNKKMFNQAMCWCTDTADAALLICEH
      ****** ******* ****. ***.*****.*.*..*..**. .**************.***
 301" ISVPRSAAKHPTDTYPDASEKSIRKAIATFLPKFTEKELFNRHLCWCTDTADAALLMCEH

359' PEWKNFVLATGDSGHSFKLLPNIGKHVVELLEGTLADDLAHAWRWRPGSGDALKSRRSAP
      ****************.*********************.***********.********.**
 361" PEWKNFVLATGDSGHTFKLLPNIGKHVVELLEGTLAEDLAHAWRWRPGTGDALKSRRAAP

419' AKDLADMPGWNHDKPRANL
      **********.**
 421" AKDLADMPGWKHDDVVKSKL
```

PROTEIN HAVING FRUCTOSYL VALYL HISTIDINE OXIDASE ACTIVITY, MODIFIED PROTEIN, AND USE OF THE PROTEIN OR THE MODIFIED PROTEIN

TECHNICAL FIELD

The present invention relates to: a glycosylated protein, particularly a protein having a fructosyl valyl histidine oxidase activity which protein is useful for measurement of glycosylated hemoglobin; a modified protein; a gene that encodes for the protein; and use of the protein, the modified protein or the gene.

BACKGROUND ART

Hemoglobin A1c (HbA1c) and glycoalbumin that are glycosylated proteins included in the blood are often measured as a glycemic control marker for diabetics. These glycosylated proteins are produced by nonenzymatic reaction of D-glucose included in the blood with an amino-acid residue that constitutes a blood protein. Therefore, these glycosylated proteins clearly reflect glucose quantity included in the blood.

Main glycosylated sites of the protein included in the blood are $\epsilon$-amino group of an internal lysine residue and $\alpha$-amino group of an amino terminal amino acid (N terminal amino acid). For example, the HbA1c is a glycosylated protein that is generated as a result of binding of D-glucose to $\alpha$-amino group of valine which is the N terminal amino acid of a hemoglobin $\beta$ chain.

Recently, there has been developed an enzymatic measurement method (hereinafter referred to as an "enzyme method") that measures the glycosylated protein included in the blood easily and in a short time. The enzyme method has been already commercialized. The use of the enzyme method allows high-throughput measurement of the glycosylated protein. The enzyme method is useful in the clinical examination field.

The enzyme method is conducted as follows. First, a protease hydrolyzes a glycosylated protein into glycosylated amino acids such as fructosyl valine, fructosyl lysine and fructosyl valyl histidine. Subsequently, such glycosylated amino acids are oxidatively hydrolyzed by use of fructosyl amino acid oxidase (FAOD). Thereafter, hydrogen peroxide generated by the oxidase reaction is colorimetrically determined by peroxidase chromogenic reaction system (see Patent Literatures 1 through 11).

In a case where the glycosylated protein is measured by the enzyme method, a substrate specificity of the fructosyl amino acid oxidase that is a main reaction enzyme is an important factor. For example, in a case where the HbA1c is measured, it is preferable to use an enzyme that has an excellent substrate specificity to fructosyl valine.

Further, in order to measure specifically to a $\beta$ chain of the glycosylated hemoglobin, it is preferable to use an enzyme that acts on fructosyl valyl histidine. This is because N terminal amino acids of an $\alpha$ chain and a $\beta$ chain of hemoglobin are both valines, and it is therefore necessary to recognize two amino acid residues at N terminal (that is, fructosyl valyl histidine) in order to measure specifically to the $\beta$ chain (see Patent Literatures 12 and 13).

A bacteria that produces an oxidase that acts on fructosyl valyl histidine has been screened so far (see, for example, Patent Literature 14).

It has been reported to use genetically modified bacteria in order to produce, extract and purify the oxidase that acts on fructosyl valyl histidine. It has been also reported isolating a gene that encodes for the oxidase (see Patent Literatures 15 and 17, and Non-Patent Literatures 1 and 2).

CITATION LIST

Patent Literature

Patent Literature 1—Japanese Patent Application Publication Tokukai No. 2004-129531 A (Publication Date: Apr. 30, 2004)

Patent Literature 2—Japanese Patent Application Publication Tokukai No. 2004-113014 A (Publication Date: Apr. 15, 2004)

Patent Literature 3—Pamphlet of International Patent Application Publication No. WO 2003/064683 (Publication Date: Aug. 7, 2003)

Patent Literature 4—Japanese Patent Application Publication Tokukai No. 2007-181466 A (Publication Date: Jul. 19, 2007)

Patent Literature 5—Japanese Patent Application Publication Tokukai No. 2007-289202 A (Publication Date: Nov. 8, 2007)

Patent Literature 6—Japanese Patent Application Publication Tokukai No. 2005-110657 A (Publication Date: Apr. 28, 2005)

Patent Literature 7—Japanese Patent Application Publication, Japanese Patent No. 4045322 (Issue Date: Feb. 13, 2008)

Patent Literature 8—Japanese Patent Application Publication, Japanese Patent No. 4014088 (Issue Date: Sep. 21, 2007)

Patent Literature 9—Japanese Patent Application Publication, Japanese Patent No. 4039664 (Issue Date: Jan. 30, 2008)

Patent Literature 10—Japanese Patent Application Publication, Japanese Patent No. 4010474 (Issue Date: Nov. 21, 2007)

Patent Literature 11—Japanese Patent Application Publication, Japanese Patent No. 3971702 (Issue Date: Sep. 5, 2007)

Patent Literature 12—International Patent Application Publication No. WO 2005/049857 booklet (Publication Date: Jun. 2, 2005)

Patent Literature 13—International Patent Application Publication No. WO 2005/049858 booklet (Publication Date: Jun. 2, 2005)

Patent Literature 14—Japanese Patent Application Publication Tokukai No. 2004-275013 A (Publication Date: Oct. 7, 2004)

Patent Literature 15—Japanese Patent Application Publication Tokukai No. 2003-235585 A (Publication Date: Aug. 26, 2003)

Patent Literature 16—Pamphlet of International Patent Application Publication No. WO 2007/010950 (Publication Date: Jan. 25, 2008)

Patent Literature 17—Pamphlet of International Patent Application Publication No. WO 2004/104203 (Publication Date: Dec. 2, 2004)

Non-Patent Literature

Non-Patent Literature 1—Arch. Microbiol., 180: 227-231 (2003)

Non-Patent Literature 2—Biochem. Biophys. Res. Commun., 311: 104-111 (2003)

SUMMARY OF INVENTION

Technical Problem

However, most of conventional fructosyl amino acid oxidases that act on fructosyl valine do not substantially act on fructosyl valyl histidine that is a substrate larger than fructosyl valine. In order to acquire a fructosyl amino acid oxidase that acts on fructosyl valyl histidine, screening with a lot of work, time and cost has been required.

Further, conventional fructosyl valyl histidine oxidases disclosed in Patent Literature 15 and Non-Patent Literatures 1 and 2 have such demerits that they are low in thermal stability and incapable of being stored in a long time in liquid clinical diagnostic agents.

Furthermore, a relatively great amount of undesirable fructosyl lysine would be undesirably produced when a glycosylated protein is hydrolyzed by a protease in the enzyme method. It is therefore preferable in the enzyme method to use a fructosyl amino acid oxidase having a low reactivity to fructosyl lysine. Patent Literature 17 discloses a keto amine oxidase. An amino acid sequence of the keto amine oxidase shares 85.5% (see FIG. 1) of homology with the amino acid sequence shown in SEQ ID NO: 1 and has 2.5% of reactivity to fructosyl lysine. The keto amine oxidase reacts with fructosyl valyl histidine. Hence, the keto amine oxidase can be referred to as a fructosyl valyl histidine oxidase. However, other enzyme properties of the fructosyl valyl histidine oxidase are unclear. Therefore, it is unclear whether or not the fructosyl valyl histidine oxidase can be used in liquid clinical diagnostic agents.

That is, it has not been developed a fructosyl valyl histidine oxidase which has both an excellent thermal stability and a low reactivity with fructosyl lysine. Hence, the conventional technique in which an oxidase is used as a liquid clinical diagnostic product has not reached a practicable level yet.

More concretely, the conventional analysis with the conventional fructosyl valyl histidine oxidase shows an extremely great measurement value in a case where an analyte is mixed with a free glycosylated amine from any cause. The above problem often occurs in, particularly, a patient given with high-calorie transfusion. It is considered that this problem is attributed to a free glycosylated amino acid or glycosylated peptide produced in the blood of the patient or in a transfusion bag in a case where a highly-concentrated sugar and amino acid are introduced into the body of the patient from the transfusion. Particularly, in case of HbA1c analysis, FAOD would react with fructosyl valine, thereby leading to extremely high glycosylated protein quantity due to introduction of fructosyl valine into the analyte.

To solve the problem, the following system has been developed. The free glycosylated amine other than an object to be measured is eliminated in advance by use of FAOD before the object to be measured undergoes reductive reaction with FAOD (see, for example, Patent Literatures 3, 5, 7 and 16).

However, the method needs to use FAOD in order to eliminate the glycosylated amine, which inevitably produces hydrogen peroxide. If the hydrogen peroxide thus produced is involved in oxidation-reduction reaction of the object to be measured, this increases a measurement value. Therefore, this method requires removal of the hydrogen peroxide before the object to be measured undergoes oxidation-reduction reaction with FAOD.

On this account, a glycosylated amine measurement method including a step of eliminating in advance the free glycosylated amine by use of FAOD includes the following reactions (1) through (4) below:

(1) reaction of eliminating a free amine by use of FAOD (hereinafter referred to as "elimination reaction");

(2) reaction of removing hydrogen peroxide produced by the elimination reaction (hereinafter referred to as "removal reaction");

(3) reaction of fragmenting a glycosylated protein into glycosylated amino acids or glycosylated peptides by use of a protease (hereinafter referred to as "fragmentation reaction")

(4) reaction of developing a color by oxidation-reduction-reaction of the fragmented glycosylated amino acids or glycosylated peptides with FAOD (hereinafter referred to as "color-developing reaction").

In the removal reaction, for example, self-condensation of a hydrogen donor and a POD (peroxidase) and/or coexistence of catalase occur. If hydrogen peroxide is not completely removed and therefore the hydrogen peroxide remains when the color-developing reaction is performed, the measurement value is possibly increased.

When performing these reactions, it is therefore necessary to perform at least the elimination reaction and the removal reaction prior to the color-developing reaction. Further, the protease that is used in the fragmentation reaction breaks down the enzyme (FAOD). It is therefore necessary to use an enzyme having an excellent resistance against the protease, or it is necessary to perform the elimination reaction and the removal reaction separately from the fragmentation reaction. As described above, the method for measuring the glycosylated amine has such a drawback that composition of a glycosylated amine measurement reagent, an addition timing of the glycosylated amine measurement reagent, and the reaction sequence are restricted.

Further, glycosylated albumin is contained in the blood sample. It is therefore necessary to eliminate influence of the glycosylated albumin in the case of HbA1c analysis. The glycosylated albumin has glycosylated ε-amino group of a lysine residue in albumin. Therefore, a measurement value becomes great in a case where FAOD reacts with fructosyl lysine produced as a result of the fragmentation by the protease. To solve the above problem, it is preferable to use FAOD reactive with fructosyl valyl histidine but poorly reactive with fructosyl valine and fructosyl lysine. However, such FAOD has not reported yet.

The present invention is made in view of the above problem, and an object of the present invention is to produce a novel glycosylated protein, particularly a novel protein having a fructosyl valyl histidine oxidase activity which novel protein is useful for measurement of glycosylated hemoglobin, a modified protein, and a gene that encodes for the protein. Further, the object of the present invention is also to provide a method for measuring a glycosylated protein such as the glycosylated hemoglobin by way of the protein, a reagent composition for measurement of the glycosylated protein such as the glycosylated hemoglobin, a kit for measuring the glycosylated protein such as the glycosylated hemoglobin, a sensor for measuring the glycosylated protein such as the glycosylated hemoglobin, and the like.

Solution to Problem

The inventors of the present invention conducted diligent studies in order to attain the object. As a result, the inventors found that a gene product derived from *Phaeosphaeria nodorum* among fructosyl amino acid oxidase homologous genes with unknown functions in a microbial genome database was a fructosyl valyl histidine oxidase that acted on fructosyl valyl histidine. The amino acid sequence of the fructosyl valyl histidine oxidase is shown in SEQ ID NO: 1.

As a result of further studies, the inventors found that the fructosyl valyl histidine oxidase had an excellent thermal stability, substrate specificity and affinity to a substance. As a result, the inventors completed the present invention.

Furthermore, as a result of further diligent studies, the inventors succeeded in acquiring a mutant protein (modified protein) having a fructosyl valyl histidine oxidase activity which protein was useful for measurement of fructosyl valyl histidine and having more improved substrate specificity and/or thermal stability than those of a wild-type protein thereof. Moreover, the inventors also confirmed that it was possible to measure a fructosyl amino acid by causing the mutant protein to act on a sample including fructosyl valyl histidine, and then quantifying resultant hydrogen peroxide by peroxidase reaction.

That is, the present invention includes the following arrangement.

A protein of the present invention, to attain the object, is a protein having a fructosyl valyl histidine oxidase activity, the protein being any one of proteins (I) through (III), below: (I) a protein comprising the amino acid sequence shown in SEQ ID NO: 1; (II) a protein comprising the amino acid sequence shown in SEQ ID NO: 1 in which one or a few amino acid residues are replaced, deleted, inserted and/or added, the protein having the fructosyl valyl histidine oxidase activity; and (III) a protein comprising an amino acid sequence having 86.0% or greater of homology with the amino acid sequence shown in SEQ ID NO: 1, the protein having the fructosyl valyl histidine oxidase activity.

It is preferable to arrange the protein of the present invention such that the protein is the protein described in (II) or (III), in which isoleucine at $58^{th}$ position from an amino terminal and/or glycine at $110^{th}$ position from the amino terminal are/is replaced with another amino acid.

It is preferable to arrange the protein of the present invention such that the protein is the protein described in (II) or (III), in which phenylalanine at $282^{th}$ position from the amino terminal is replaced with another amino acid.

It is preferable to arrange the protein of the present invention such that the isoleucine at $58^{th}$ position from the amino terminal is replaced with methionine, threonine, alanine, asparagine, serine, valine or leucine.

It is preferable to arrange the protein of the present invention such that the glycine at $110^{th}$ position from the amino terminal is replaced with glutamine, methionine, glutamic acid, threonine, alanine, cysteine, histidine, lysine, asparagine, arginine, serine, valine, leucine, asparagine acid, isoleucine, tyrosine or phenylalanine.

It is preferable to arrange the protein of the present invention such that the phenylalanine at $282^{th}$ position from the amino terminal is replaced with tyrosine.

A polynucleotide of the present invention, in order to attain the object, is a polynucleotide that encodes for a protein having a fructosyl valyl histidine oxidase activity, the polynucleotide being any one of polynucleotides (IV) through (VII), below: (IV) a polynucleotide comprising the nucleotide sequence shown in SEQ ID NO: 2; (V) a polynucleotide comprising the nucleotide sequence shown in SEQ ID NO: 2 in which 1 through 30 nucleotides are replaced, deleted, inserted and/or added, the polynucleotide encoding for the protein having the fructosyl valyl histidine oxidase activity; (VI) a polynucleotide that encodes for any one of the proteins of the present invention; and (VII) a polynucleotide that hybridizes, under a stringent condition, with a polynucleotide comprising a nucleotide sequence complementary to that of any one of the polynucleotides (IV) through (VI), the polynucleotide encoding for the protein having the fructosyl valyl histidine oxidase activity.

It is preferable that 1 through 20 nucleotides of the protein (II) are replaced, deleted, inserted and/or added.

Further, the present invention provides: a recombinant vector including any one of the polynucleotides of the present invention; and a transformant that is transformed from a host by use of the recombinant vector.

A method for producing a protein of the present invention, in order to attain the object, including the steps of: culturing the transformant so that the protein having the fructosyl valyl histidine oxidase activity is produced; and collecting the protein.

A method for measuring a glycosylated protein of the present invention, in order to attain the object, including the step of causing any one of the proteins of the present invention to act on a glycosylated amine.

A method for measuring glycosylated hemoglobin of the present invention, in order to attain the object, including the steps of: preparing a glycosylated amine from glycosylated hemoglobin included in a sample; and causing any one of the proteins of the present invention to act on the sample. According to the measurement method, it is possible to confirm whether or not the glycosylated hemoglobin is included in the sample and to measure the amount of the glycosylated hemoglobin.

The step of preparing the glycosylated amine can be conducted by degrading the glycosylated hemoglobin into peptide fragments of a suitable length(s) or degrading the glycosylated hemoglobin into amino acids. Further, it is preferable that the glycosylated amine thus prepared includes at least one selected from the group consisting of fructosyl valine, fructosyl valyl histidine and glycosylated peptides having fructosyl valyl histidyl group at an end thereof, more preferably includes fructosyl valyl histidine and/or glycosylated peptides having the fructosyl valyl histidine group at the end so that it is possible to individually measure an α chain and a β chain of hemoglobin.

Further, the present invention provides: a kit for measuring a glycosylated protein; and a sensor for measuring the glycosylated protein, the kit and the sensor each including any one of the proteins of the present invention.

The inventors conducted diligent studies on *Phaeosphaeria nodorum* genome information (see http://genamics.com/cgi-bin/genamics/genomes/genomesearch.cgi?field=ID&query=1666). As a result of the studies, the inventors found that *Phaeosphaeria nodorum* could produce the fructosyl valyl histidine oxidase. Further, the inventors more deeply studied on *Phaeosphaeria nodorum*, based on the findings. As a result of the deep study, the inventors succeeded in expressing, from a gene of *Phaeosphaeria nodorum*, the fructosyl valyl histidine oxidase (amino acid sequence thereof is shown in SEQ ID NO: 1) that acts on fructosyl valyl histidine.

On the basis of homology search of a genome sequence that has been already found, it is possible to predict to some extent that a protein having the amino acid sequence shown in SEQ ID NO: 1 (hereinafter referred to as a "protein of SEQ ID NO: 1" as appropriate) will possibly produce a fructosyl amino acid oxidase. However, it is impossible to find from the genome information and amino acid sequence information whether or not the fructosyl amino acid oxidase (that is, "fructosyl valyl histidine oxidase") acts on fructosyl valyl histidine. Further, the three dimensional structure of the fructosyl amino acid oxidase has not found out yet. It is therefore impossible to predict the enzyme activity of the fructosyl amino acid oxidase from the three dimensional structure information. Furthermore, there have been many reports to report that a protein expressed from a gene selected via homology search and then cloned was impossible to be purified or did not have an enzyme activity as predicted.

Advantageous Effects of Invention

The present invention makes it possible to provide a glycosylated protein, particularly a fructosyl valyl histidine oxidase agent that is useful for measurement of glycosylated hemoglobin, and use of the agent. The present invention also makes it possible to provide a protein having a fructosyl valyl histidine oxidase activity which protein has an excellent thermal stability, substrate specificity and affinity to a substance, and use of the protein.

Further, the present invention yields an effect of providing a modified fructosyl valyl histidine oxidase that has more excellent substrate specificity and/or thermal stability. More concretely, according to the present invention, it is possible to further improve the protein in terms of the substrate specificity to fructosyl valyl histidine by replacing, with another amino acid, isoleucine at $58^{th}$ position from an amino terminal of a protein comprising the amino acid sequence shown in SEQ ID NO: 1. It is also possible to further improve the protein in terms of the thermal stability by replacing, with another amino acid, glycine at $110^{th}$ position from the amino terminal. This allows more precise measurement of glycosylated protein quantity.

BRIEF DESCRIPTION OF DRAWINGS

FIG. 1 shows that homology of an amino acid sequence of a fructosyl valyl histidine oxidase derived from *Phaeosphaeria nodorum* is compared with that of an amino acid sequence of a fructosyl valyl histidine oxidase derived from *Curvlaria claveta*.

DESCRIPTION OF EMBODIMENTS

The following describes in detail an embodiment of the present invention. However, the present invention is not limited to this embodiment. Note that all of Non-Patent Literatures and Patent Literatures described in this specification are incorporated in this specification by way of references. Further, in this specification, "••• through •••" means "••• and above, and ••• and below". For example, "A value through B value" in this specification indicates "A value and above" and "B value and below". Furthermore, "and/or" in this specification means "either" or "both".

1. Protein of the Present Invention

A protein of the present invention is a protein having a fructosyl valyl histidine oxidase activity, and is any one of proteins (I) through (III) below:

(I) a protein comprising the amino acid sequence shown in SEQ ID NO: 1;

(II) a protein comprising the amino acid sequence shown in SEQ ID NO: 1 in which one or a few amino acid residues are replaced, deleted, inserted and/or added, the protein having the fructosyl valyl histidine oxidase activity; and (III) a protein comprising an amino acid sequence having 86.0% or greater of homology with the amino acid sequence shown in SEQ ID NO: 1, the protein having the fructosyl valyl histidine oxidase activity.

The amino acid sequence shown in SEQ ID NO: 1 is an amino acid sequence of a fructosyl valyl histidine oxidase, the amino acid sequence being searched out from the *Phaeosphaeria nodorum* genome database (http://www.ncbi.nlm.nih.gov/entrez/viewer.fcgi?db=nucleotide &val=NZ_AAGI00000000), and then isolated.

The present invention encompasses the protein comprising the aforementioned amino acid sequence in which one or more amino acids are replaced, deleted, inserted and/or added, the protein having the fructosyl valyl histidine oxidase activity. The replacement, deletion, insert and/or addition of the one or more amino acids may be at any sites of the amino acid sequence as along as a resultant protein after the replacement, deletion, insert and/or addition of the amino acids has the fructosyl valyl histidine oxidase activity. More specifically, the "one or a few amino acid residues" are 10 or less amino acid residues. Preferably, the "one or a few amino acid residues" are 6 or less amino acid residues.

Further, the present invention encompasses the protein comprising an amino acid sequence having 86.0% or greater, preferably 90.0% or greater, more preferably 95.0% or greater of homology with the amino acid sequence (shown in SEQ ID NO: 1). The protein of the present invention also has the fructosyl valyl histidine oxidase activity.

The homology of the amino acid sequence can be calculated by a conventional method. Concretely, the homology of the amino acid sequence is percentage (%) as to how much the amino acid sequence is homologous with the amino acid sequence shown in SEQ ID NO: 1 and is calculated by homology search conducted by use of GENETYX-WIN (product name; manufactured by GENETYX Co., Ltd.) according to a manual thereof. The homology can be determined by comparing two sequences that are aligned over whole regions thereof as much as possible. To align nucleotide sequences or amino acid sequences as much as possible for comparison, for example, the nucleotide sequences or the amino acid sequences may be modified by addition or deletion (for example, addition of a gap, or the like).

It is preferable that isoleucine at $58^{th}$ position from an amino terminal of the amino acid sequence shown in SEQ ID NO: 1 and/or glycine at $110^{th}$ position from the amino terminal of the amino acid sequence shown in SEQ ID NO: 1 are/is replaced with other amino acids, respectively, the isoleucine and the glycine being included in the "protein comprising the amino acid sequence shown in SEQ ID NO: 1 in which one or a few amino acid residues are replaced, deleted, inserted and/or added, the protein having the fructosyl valyl histidine oxidase activity" or the "protein comprising an amino acid sequence having 86.0% or greater of homology with the amino acid sequence shown in SEQ ID NO: 1, the protein having the fructosyl valyl histidine oxidase activity".

According to the above-described protein, the isoleucine at $58^{th}$ position from the amino terminal and/or the glycine at $110^{th}$ position from the amino terminal are/is replaced with other amino acids, respectively. The other amino acids are not particularly limited. The isoleucine and the glycine at their positions can be replaced with conventional amino acids as appropriate. Examples of the amino acids to replace the isoleucine and the glycine at their positions encompass a basic amino acid constituting a natural protein, a modified amino acid that is chemically modified, and a special amino acid that is derived from the basic amino acid. However, the amino acids to replace the isoleucine and the glycine at their positions are not limited to these examples.

If the isoleucine at $58^{th}$ position from the amino terminal is replaced with another amino acid, this makes it possible to further improve the protein in terms of a substrate specificity to fructosyl valyl histidine. Further, if the glycine at 110$^{th}$ position from the amino terminal is replaced with another amino acid, this makes it possible to further improve the protein in terms of a thermal stability.

First, the following concretely describes the case where the isoleucine at 58$^{th}$ position from the amino terminal is replaced with another amino acid.

It is preferable that the isoleucine at 58$^{th}$ position from the amino terminal is replaced with, for example, methionine, threonine, alanine, asparagine, serine, valine or leucine. The above replacement makes it possible to further improve the substrate specificity (a reactivity to fructosyl valyl histidine) of the fructosyl valyl histidine oxidase.

It is more preferable that the isoleucine at 58$^{th}$ position from the amino terminal is replaced with threonine, serine, valine or alanine for the sake of further improving the substrate specificity to fructosyl valyl histidine (in other words, improving the protein to have lower reactivities to both fructosyl valine and fructosyl lysine as substrates).

Further, it is more preferable that the isoleucine at 58$^{th}$ position from the amino terminal is replaced with methionine, serine or alanine for the sake of improving not only the substrate specificity but also the thermal stability.

Accordingly, it is most preferable that the isoleucine at 58$^{th}$ position from the amino terminal is replaced with serine or alanine for the sake of further improving not only the substrate specificity but also the thermal stability.

In the case of the protein in which the isoleucine at 58$^{th}$ position from the amino terminal is replaced with another amino acid, any sites other than 58$^{th}$ position from the amino terminal may also be replaced, deleted, inserted and/or added. In this case, the sites other than 58$^{th}$ position from the amino terminal and at which the replacement, deletion, insertion and/or addition takes place are not particularly limited.

The following concretely describes a case where the glycine at 110$^{th}$ position from the amino terminal is replaced with another amino acid.

It is preferable that the glycine at 110$^{th}$ position from the amino terminal is replaced with an amino acid other than tryptophan and proline. More specifically, it is preferable that the glycine at 110$^{th}$ position from the amino terminal is replaced with glutamine, methionine, glutamic acid, threonine, alanine, cysteine, histidine, lycine, asparagine, arginine, serine, valine, leucine, asparagine acid, isoleucine, tyrosine or phenylalanine. The above replacement makes it possible to improve the thermal stability of the fructosyl valyl histidine oxidase.

It is more preferable that the glycine at 110$^{th}$ position from the amino terminal is replaced with glutamic acid (E), alanine (A), valine (V) or tyrosine (Y) for the sake of improving not only the thermal stability but also a specific activity.

Further, it is more preferable that the glycine at 110$^{th}$ position is replaced with histidine (H), leucine (L), isoleucine (I), tyrocine (Y) or phenylalanine (F) for the sake of improving not only the thermal stability but also a Km value.

Furthermore, it is more preferable that the glycine at 110$^{th}$ position from the amino terminal is replaced with glutamic acid (E) or asparagine acid (D) for the sake of improving not only the thermal stability but also the substrate specificity.

In the case where the glycine at 110$^{th}$ position from the amino terminal is replaced with another amino acid, any sites other than 110$^{th}$ position from the amino terminal can also be replaced, deleted, inserted and/or added. In this case, the sites other than 110$^{th}$ position from the amino terminal and at which the replacement, deletion, insertion and/or addition takes place are not particularly limited.

As described above, it is preferable that the 58$^{th}$ amino acid and 110$^{th}$ amino acid from the amino terminal of the amino acid sequence shown in SEQ ID NO: 1 are both replaced with other amino acids, respectively. According to the replacement, it is possible not only to improve the thermal stability of the fructosyl valyl histidine oxidase but also to decrease the reactivity to fructosyl lysine. Further, as described above, the amino acid with which the glycine at 110$^{th}$ position from the amino terminal is replaced is not particularly limited. It is preferable that the amino acid with which the glycine at 110$^{th}$ position is replaced is, for example, glutamine. In the case where the glycine at 110$^{th}$ position is replaced with glutamine, it is possible to further decrease the reactivity to fructosyl valine and fructosyl lysine.

Further, it is preferable that not only the 58$^{th}$ amino acid and 110$^{th}$ amino acid from the amino terminal of the amino acid sequence shown in SEQ ID NO: 1 but also phenylalanine at 282$^{th}$ position from the amino terminal is replaced with another amino acid, the phenylalanine being included in the "protein comprising the amino acid sequence shown in SEQ ID NO: 1 in which one or a few amino acid residues are replaced, deleted, inserted and/or added, the protein having the fructosyl valyl histidine oxidase activity" or the "protein comprising an amino acid sequence having 86.0% or greater of homology with the amino acid sequence shown in SEQ ID NO: 1, the protein having the fructosyl valyl histidine oxidase activity". The above replacement makes it possible to improve the thermal stability of the fructosyl valyl histidine oxidase.

The amino acid with which the phenylalanine at 282$^{th}$ position from the amino terminal is replaced is not particularly limited. One preferable example of the amino acid with which the phenylalanine at 282$^{th}$ position is replaced is tyrosine. In the case where the phenylalanine at 282$^{th}$ position is replaced with tyrosine, it is possible to further improve the thermal stability of the fructosyl valyl histidine oxidase.

The fructosyl valyl histidine oxidase activity of the present invention is measured by a method later described in "activity measurement method" in Examples. The fructosyl valyl histidine oxidase activity may be measured by using fructosyl valyl histidine as a substrate. What is meant by the phrase "having the fructosyl valyl histidine oxidase activity" in the present invention is at least to have an oxidase activity attained by fructosyl valyl histidine serving as a substrate. Preferably, the oxidase activity is 0.1 U/mg-protein or greater, more preferably 1.0 U/mg-protein or greater. Further, the protein of the present invention may include not only the fructosyl valyl histidine oxidase activity but also another enzyme activity (which may be, but not limited to, an oxidase activity to fructosyl valine, for example).

The protein of the present invention may be produced from, for example, an organism (such as bacteria, yeasts, insects, nematode, zebra fish and mammals) which produces the protein of the present invention and which is isolated from the nature. That is, the protein of the present invention encompasses proteins produced by various organisms. Further, the protein of the present invention may be produced by gene recombination technology, or may be chemically synthesized by use of an amino acid synthesizer or the like. Examples of recombinant protein expression systems suitably employed in the gene recombination technology encompass *Escherichia coli* expression system, insect cell expression system, mammal cell expression system and cell-free expression system. However, these are not the only options. A method for producing the protein of the present invention is described later.

Further, examples of the protein of the present invention encompass, but not limited to: an intermolecularly cross-linked and/or intramolecularly cross-linked protein (for example, disulfide bond); a chemically modified protein (for example, with a sugar chain, phosphoric acid or other functional group); a labeled protein (for example, the protein labeled with a histidine tag, a Myc tag, a Flag tag, or the like); and a protein to which a fusion protein (for example, a streptavidin, a cytochrome, a GST, a GFP, or the like) is added. Furthermore, the protein of the present invention may be a chimeric protein comprising fragments of various proteins as long as the chimeric protein has the fructosyl valyl histidine oxidase activity.

Further, a fructosyl valyl histidine oxidase agent may comprise the protein of the present invention, and a diluting agent such as a serum protein, an organic acid, or dextran. The fructosyl valyl histidine oxidase agent may also include a conventional material serving as a component of an enzyme preparation.

2. Polynucleotide of the Present Invention

A polynucleotide of the present invention is characterized in being a polynucleotide that encodes for the protein of the present invention.

The polynucleotide of the present invention is a polynucleotide which is any one of the following polynucleotides (IV) through (VII) and which encodes for the protein having the fructosyl valyl histidine oxidase activity. The polynucleotides (IV) through (VII) are:

(IV) a polynucleotide comprising the nucleotide sequence shown in SEQ ID NO: 2;

(V) a polynucleotide comprising the nucleotide sequence shown in SEQ ID NO: 2 in which 1 through 30 nucleotides are replaced, deleted, inserted and/or added, the polynucleotide encoding for the protein having the fructosyl valyl histidine oxidase activity;

(VI) a polynucleotide that encodes for the protein of the present invention; and (VII) a polynucleotide that hybridizes, under a stringent condition, with a polynucleotide comprising a nucleotide sequence complementary to that of any one of the polynucleotide (IV) through (VI), the polynucleotide encoding for the protein having the fructosyl valyl histidine oxidase activity.

The term "polynucleotide" used in the present specification is used so as to be exchangeable with a "gene", a "nucleic acid" or a "nucleic-acid molecule", and means a polymer of a nucleotide. The polynucleotide can be in the form of DNA (for example, cDNA or genome DNA) or RNA (for example, mRNA). The DNA or RNA may be double strand or a single-strand. The single-strand DNA or RNA may be a coding strand (sense strand) or a noncoding strand (antisense strand).

Further, the polynucleotide of the present invention may be chemically synthesized, and codon usage of the polynucleotide may be modified so as to improve expression of the protein to be encoded. As a matter of course, it is possible to replace a codon with another codon if the codon and the another codon both encode for an identical amino acid.

A method for producing the polynucleotide of the present invention is not particularly limited. The polynucleotide of the present invention can be produced by a conventional method as appropriate. For example, the polynucleotide of the present invention can be produced by introducing, as appropriate, mutation into the polynucleotide (SEQ ID NO: 2) that encodes for a wild-type fructosyl valyl histidine oxidase. The polynucleotide of the present invention can also be produced by a chemical synthesis method.

Further, the polynucleotide of the present invention is produced by a conventional method for modifying a polynucleotide. That is, it is possible to produce a polynucleotide having genetic information of a desirable recombinant protein by replacing, deleting, inserting and/or adding a specific nucleotide in the polynucleotide having the genetic information of the protein. Concretely, the nucleotide in the polynucleotide is modified by use of commercially available kits such as a KOD-Plus Site-Directed Mutagenesis Kit manufactured by TOYOBO Co., Ltd., a Transformer Site-Directed Mutagenesis Kit manufactured by Clonetech Corporation, and a QuickChange Site Directed Mutagenesis Kit manufactured by Stratagene Corporation, or by polymerase chain reaction (PCR). The above-described methods are well-known to a person skilled in the art.

The nucleotide sequence of the polynucleotide of the present invention is not particularly limited as long as the polynucleotide of the present invention encodes for the protein of the present invention. Therefore, the polynucleotide of the present invention encompasses all polynucleotides each comprising a nucleotide sequence corresponding to the amino acid sequence of the protein of the present invention.

The polynucleotide of an embodiment of the present invention may be a polynucleotide in which a part of nucleotides constituting the polynucleotide of the present invention are replaced with a chemically synthesized nucleotide (that is, normative nucleotides). Further, a site where the polynucleotide of the present invention is replaced is not particularly limited as long as a protein expressed from the replaced nucleotide sequence has a suitable property.

The polynucleotide of the present invention may comprise just the polynucleotide that encodes for the protein of the present invention, and may also have other nucleotide sequence added thereto. The nucleotide sequence to be added is not limited. Examples of the nucleotide sequence to be added encompass nucleotide sequences that encode for a labeled protein (for example, the protein labeled with a histidine tag, a Myc tag, a FLAG tag or the like), a fusion protein (for example, a streptavidin, a cytochrome, a GST, a GFP or a MBP), a promoter sequence (for example, a promoter sequence derived from a yeast, a promoter sequence derived from a phage, or a promoter sequence derived from *Escherichia coli*), and a signal sequence (for example, an ER export signal sequence and a secretory sequence). Sites to which these nucleotide sequences are added are not particularly limited. For example, the sites may be an N terminal or a C terminal of a protein to be translated.

The polynucleotide of the present invention may be the polynucleotide that encodes for the protein of the present invention (for example, the polynucleotide including the nucleotide sequence shown in SEQ ID NO: 2), or the polynucleotide that hybridizes, under a stringent condition, with the polynucleotide comprising the nucleotide sequence complementary to that of the polynucleotide of the present invention.

Here, what is meant by the "stringent condition" is a condition under which hybridization occurs at a temperature that is 15° C., preferably 10° C., more preferably 5° C. lower than a melting temperature (Tm value) of nucleic acids having a great homology with each other, for example, hybrids whose homology is completely identical. For example, the condition is a condition under which hybridization occurs at 68° C. for 20 hours in a general hybridization buffer solution. More concretely, the hybridization occurs by a conventional method described in Molecular Cloning, A Laboratory Manual, 2d Ed., Cold Spring Harbor Laboratory (1989) authored by Sambrook and like authors.

The nucleotide sequence of the polynucleotide of the present invention can be determined by a dideoxy method described in Science, 214: 1205 (1981).

The following describes an example of the polynucleotide of the present invention in further detail. However, the present invention is not limited to this example. The polynucleotide of the present invention includes polynucleotides produced by various combinations of replacement described later.

First, the following describes, as an example of the present invention, a polynucleotide that encodes for an amino acid sequence in which isoleucine at $58^{th}$ position from the amino terminal of the amino acid sequence shown in SEQ ID NO: 1 is replaced with another amino acid.

It is preferable that the polynucleotide of the present invention is, for example, the polynucleotide that encodes for the amino acid sequence in which the isoleucine at $58^{th}$ position from the amino terminal of the amino acid sequence shown in SEQ ID NO: 1 is replaced with another amino acid. More concretely, it is preferable that the polynucleotide of the present invention is a polynucleotide shown in SEQ ID NO: 2 in which polynucleotide "att ($172^{th}$ nucleotide through $174^{th}$ nucleotide)" is replaced with a codon that encodes for an amino acid other than isoleucine.

The codon with which the "att" is replaced is not particularly limited. Examples of the codon encompass a codon that encodes for methionine, threonine, alanine, asparagine, serine, valine or leucine. More concretely, it is preferable that the "att" is replaced with "atg (a codon that encodes for methionine)", "acc (a codon that encodes for threonine)", "gct (a codon that encodes for alanine)", "aac (a codon that encodes for asparagine), "tcg (a codon that encodes for serine)", "gtc (a codon that encodes for valine)" or "ctc (a codon that encodes for leucine)". However, these are not the only options. As a matter of course, it is also possible to replace the "att" with another codon that encodes for the amino acid.

In addition to the above-described replacement, it is preferable that the polynucleotide of the present invention is also a polynucleotide that encodes for an amino acid sequence in which the phenylalanine at $282^{th}$ position from the amino terminal of the amino acid sequence shown in SEQ ID NO: 1 is replaced with another amino acid. More concretely, it is preferable that the polynucleotide of the present invention is the polynucleotide shown in SEQ ID NO: 2 in which polynucleotide "ttc ($844^{th}$ nucleotide through $846^{th}$ nucleotide)" is replaced with a codon that encodes for an amino acid other than phenylalanine.

The codon with which the "ttc" is replaced is not particularly limited. It is preferable that the codon with which the "ttc" is replaced is, for example, a codon that encodes for tyrosine. More concretely, it is preferable that the "ttc" is replaced with "tat (a codon that encodes for tyrosine)". However, this is not the only option. As a matter of course, the "ttc" can be replaced with another codon that encodes for tyrosine.

In addition to the above-described replacement, it is more preferable that the polynucleotide of the present invention is a polynucleotide that encodes for an amino acid sequence in which glycine at $110^{th}$ position from the amino terminal of the amino acid sequence shown in SEQ ID NO: 1 is replaced with another amino acid. More concretely, it is preferable that the polynucleotide of the present invention is the polynucleotide shown in SEQ ID NO: 2 in which polynucleotide "gga ($328^{th}$ nucleotide through $330^{th}$ nucleotide)" is replaced with a codon that encodes for an amino acid other than glycine.

The codon with which the "gga" is replaced is not particularly limited. It is preferable that the codon with which the "gga" is replaced is, for example, a codon that encodes for glutamine. More concretely, it is preferable that the "gga" is replaced with "cag (a codon that encodes for glutamine)". However, this is not the only option. As a matter of course, the "gga" can be replaced with another codon that encodes for glutamine.

The following describes, as an example of the present invention, a polynucleotide that encodes for an amino acid sequence in which the glycine at $110^{th}$ position from the amino terminal of the amino acid sequence shown in SEQ ID NO: 1 is replaced with another amino acid.

As described above, it is preferable that the polynucleotide of the present invention is the polynucleotide that encodes for the amino acid sequence in which the glycine at $110^{th}$ position from the amino terminal of the amino acid sequence shown in SEQ ID NO: 1 is replaced with another amino acid. More concretely, it is preferable that the polynucleotide of the present invention is the polynucleotide shown in SEQ ID NO: 2 in which polynucleotide "gga ($328^{th}$ nucleotide through $330^{th}$ nucleotide)" is replaced with a codon that encodes for an amino acid other than glycine.

The codon with which the "gga" is replaced is not particularly limited. It is preferable that the codon with which the "gga" is replaced is, for example, a codon that encodes for an amino acid other than tryptophan and proline. More concretely, it is preferable that the codon with which the "gga" is replaced is a codon that encodes for glutamine, methionine, glutamic acid, threonine, alanine, cysteine, histidine, lycine, asparagine, arginine, serine, valine, leucine, asparagine acid, isoleucine, tyrosine or phenylalanine. More concretely, it is preferable that the "gga" is replaced with "acg (a codon that encodes for threonine)", "gcg (a codon that encodes for alanine)", "gtg (a codon that encodes for valine)", "ctg (a codon that encodes for leucine)", "att (a codon that encodes for isoleucine)", "atg (a codon that encodes for methionine)", "ttc (a codon that encodes for phenylalanine)", "tcc (a codon that encodes for serine)", "cag (a codon that encodes for glutamine)", "tgt (a codon that encodes for cysteine)", "tac (a codon that encodes for tyrosine)", "aac (a codon that encodes for asparagine)", "aag (a code that encodes for lycine)", "cac (a codon that encodes for histidine)", "agg (a codon that encodes for arginine)", "gac (a codon that encodes for asparagine acid)", or "gag (a codon that encodes for glutamic acid)". However, these are not the only options. As a matter of course, the "gga" can be replaced with another codon that encodes for the amino acid (replaced amino acid).

In addition to the above-described replacement, it is more preferable that the polynucleotide of the present invention is a polynucleotide that encodes for an amino acid sequence in which phenylalanine at $282^{th}$ position from the amino terminal of the amino acid sequence shown in SEQ ID NO: 1 is replaced with another amino acid. More concretely, it is preferable that the polynucleotide of the present invention is the polynucleotide shown in SEQ ID NO: 2 in which polynucleotide "ttc ($844^{th}$ nucleotide through $846^{th}$ nucleotide)" is replaced with a codon that encodes for an amino acid other than phenylalanine.

The codon with which the "ttc" is replaced is not particularly limited. It is preferable that the codon with which the "ttc" is replaced is, for example, a codon that encodes for tyrosine. More concretely, it is preferable that the "ttc" is replaced with "tat (a codon that encodes for tyrosine)". However, this is not the only option. As a matter of course, the "ttc" can be replaced with another codon that encodes for tyrosine.

3. Recombinant Vector and Transformant of the Present Invention

A vector of the present invention includes the polynucleotide of the present invention. A composition of the vector is not particularly limited as long as the vector of the present invention includes the polynucleotide of the present invention.

The vector of the present invention may be prepared from a base vector selected as suitable for a host. Examples of the base vector encompass a plasmid, a phage, a cosmid, an adenovirus and a retrovirus. However, the present invention is not limited to these.

In a case where the plasmid vector is employed as the vector of the present invention, a pBluescript (registered trademark), a pUC18 or the like can be employed as the vector of the present invention. In this case, examples of the host into which the vector is introduced encompass yeasts, *Escherichia coli* (for example, *Escherichia coli* W3110, *Escherichia coli* C600, *Escherichia coli* JM109, and *Escherichia coli* DH5α), an insect cell, a mammalian cell and the like. These hosts can be employed.

More concretely, the following hosts can be employed as the host of the present invention. They are: bacteria such as *Escherichia coli*; yeasts such as *Saccharomyces cerevisiae* and *Schizosaccharomyces pombe*; an insect cell; nematodes such as *Caenorhabditis elegans*; an oocyte of a platanna such as *Xenopus laevis*; mammalian cells such as a CHO cell, a COS cell and a Bowes melanoma cell; and various human cultured cells. Note that the present invention is not limited to these. Further, the term "transformant" described in the present specification encompasses not only a cell, a tissue or an organ but also an individual organism.

The vector of the present invention can include an expression control region (for example, a promoter, a terminator and/or a replication origin) while depending on the host into which the vector is introduced. Examples of the promoter are viral promoters such as a SV40 early promoter and a SV40 late promoter. However, the present invention is not limited to these.

The vector preferably includes at least one selection marker. Examples of the selection marker encompass an ampicilline-resistant gene, a dihydrofolate reductase and a neomycin-resistant gene. The use of the selection marker makes it possible to confirm whether or not the polynucleotide of the present invention is introduced into the host and whether or not the polynucleotide of the present invention is certainly expressed within the host.

A method for introducing the vector of the present invention into the host is not particularly limited. Examples of the method encompass conventionally well-known methods such as an electroporation, a calcium phosphate transfection, a liposome transfection and a DEAE dextran transfection. These methods are suitably employed. More concretely, in a case where the vector is introduced into a host that belongs to *Escherichia*, a method for introducing a recombinant DNA in the presence of calcium ions, or the electroporation can be conducted. Further, gene introduction may be conducted by use of a commercial competent cell (for example, a competent high JM109 and a competent high DH5α manufactured by TOYOBO Co., Ltd.).

The vector of the present invention is produced as follows. First, the polynucleotide (gene) of the present invention is isolated and purified. Subsequently, (i) fragments of the polynucleotide cut by use of a restriction enzyme or the like and (ii) a linear polynucleotide obtained by cutting the base vector by use of the restriction enzyme are bound and closed each other. In order to bind and close the fragments and the linear polynucleotide, a DNA ligase or the like can be used according to properties of the vector and the polynucleotide. The transformant including the polynucleotide (gene) of the present invention is produced by introducing the vector of the present invention into a replicable host and then screening the replicable host into which the vector of the present invention has been introduced by using, as indicators, a vector marker and expression of an enzyme activity. Accordingly, the vector of the present invention may include a marker gene such as a drug-resistant gene.

Further, the transformant of the present invention may be a transformant transformed by the vector of the present invention. The host transformed by the vector of the present invention is not particularly limited. Examples of the transformed host encompass yeasts, *Escherichia coli*, an insect cell and a mammalian cell as described above.

4. Method for Producing Protein of the Present Invention

A method for producing a protein of the present invention is characterized in including a step for culturing the transformant of the present invention (hereinafter referred to as "culturing step"). The method for producing the protein of the present invention may include other steps for producing the protein by use of the transformant in addition to the culturing step. Examples of the other steps encompass a step for collecting the protein produced by the transformant of the present invention and a step for purifying the collected protein, these steps following the culturing step.

(4-1) Culturing Step

In the culturing step, the transformant of the present invention is cultured in a nutrient culture medium or the like. This makes it possible to stably produce a great number of recombinant proteins. How to culture the transformant, that is, a culturing method, a culturing condition, etc. may be selected in consideration of nutritional and physiological properties of the host. The transformant of the present invention is often cultured in a liquid culture medium. Further, it is industrially favorable that the transformant of the present invention is cultured under aerobic condition with stirring.

A source generally used for culture is often used as a source for the nutrient culture medium used in the culturing step. An example of the source is a carbon source. As the carbon source, a carbon compound serving as the source for the nutrient culture medium is employed. Examples of the carbon compound encompass glucose, sucrose, lactose, lactose, maltose, syrup and pyruvic acid. Another example of the source is a nitrogen source. As the nitrogen source, a nitrogen compound serving as the source for the nutrient culture medium is employed. Examples of the nitrogen compound encompass peptone, a meat extract, a yeast extract, a casein hydrolysate and a soybean waste alkaline extract. In addition to these, salts such as: phosphate; carbonate; sulfate; magnesium; calcium; potassium; iron; manganese; and zinc, a specific amino acid, a specific vitamin, and the like may be added to the nutrient culture medium as appropriate.

A culture temperature of the transformant of the present invention can be modified as appropriate as long as the transformant can produce the protein of the present invention. In a case where the host is *Escherichia coli*, the culture temperature preferably ranges substantially from 20° C. to 42° C. More preferably, the culture temperature ranges from 20° C. to 30° C. It is possible to produce a great number of proteins having an activity in a case where the transformant of the present invention is cultured at the above-described culture temperature.

Culturing the transformant of the present invention may be terminated at any time when a maximum number of proteins have been produced. The culture period usually ranges substantially from 6 hours to 48 hours. Further, pH of the culture medium can be modified as appropriate as long as the transformant of the present invention suitably grows and can produce the protein of the present invention. The pH of the culture medium preferably ranges substantially from pH 6.0 to pH 9.0.

(4-2) Collecting Step

In the collecting step, the protein of the present invention produced by the transformant in the culturing step is collected.

In a case where the transformant of the present invention secretes a protein outside a cell, a culture produced by culturing the transformant includes the protein of the present invention. It is therefore possible to use the culture as the protein of the present invention itself. At this time, the transformant of the present invention may be separated from a culture solution included in the culture by means of, for example, filtration or centrifugal separation.

Further, in a case where the protein of the present invention is present within the transformant, the transformant is collected from the culture produced by culturing the transformant by means of filtration, centrifugal separation or like method, and the collected transformant is then disrupted by a mechanical process or an enzymatic method employing lysozyme or the like. In this manner, a target protein is collected. The target protein may be separated and collected in a solution by adding, as appropriate, a chelating agent such as an EDTA, and a surface-active agent such as a Triton-X100 to the transformant including the protein of the present invention so that the protein of the present invention is solubilized.

(4-3) Purifying Step

In the purifying step, the protein collected in the collecting step is purified.

How to conduct the purifying step is not particularly limited. The protein may be purified by means of, for example, vacuum concentration, membrane concentration, salting-out of a solution including the protein of the present invention (by use of, for example, ammonium sulfate or sodium sulfate), or by fractional precipitation conducted by use of a hydrophilic organic solvent such as methanol, ethanol and acetone. The above-described method makes it possible to precipitate and purify the target protein of the present invention.

Further, the purifying step may be conducted by means of heat treatment, isoelectric focusing, gel filtration, absorption chromatography, ion exchange chromatography, affinity chromatography, reverse-phase chromatography, or by combining the above-described means.

Furthermore, it is preferable that the purified enzyme including the target protein attained by the foregoing methods is purified by electrophoresis (SDS-PAGE) so as to show a single band.

The purified enzyme can be commercialized in a powder form prepared by means of, for example, freeze-dry, vacuum-dry or spray-dry. Further, the purified enzyme can be used in a state of being dissolved in a buffer solution, as appropriate according to the usage of the purified enzyme. Examples of the buffer solution encompass a borate buffer, a phosphate buffer, a Tris buffer and a GOOD buffer. These buffers are suitably used according to properties of the target protein and/or an experimental condition or circumstance. Furthermore, it is possible to stabilize the protein by adding, for example, an amino acid (for example, glutamic acid, glutamine or lysine), serum albumin and the like to the purified enzyme.

5. Method for Measuring Glycosylated Protein of the Present Invention

The method for measuring the glycosylated protein of the present invention (hereinafter referred to as a "measurement method of the present invention") causes the protein (or a fructosyl valyl histidine oxidase agent) of the present invention to act on at least a glycosylated amine. The following describes an embodiment of the measurement method of the present invention. However, the present invention is not limited to this embodiment. Further, the "protein of the present invention" described in this section can be substituted for the "fructosyl valyl histidine oxidase agent of the present invention".

The embodiment of the measurement method of the invention is the method for measuring the glycosylated protein, the method including the steps of:

(1) reacting a sample with a protease so that the glycosylated protein present in the sample is dissolved, thereby adjusting a glycosylated amine derived from the glycosylated protein present in the sample (hereinafter referred to as a "first step" for easy explanation);

(2) causing the protein of the present invention to act on the glycosylated amine derived from the glycosylated protein present in the sample, the glycosylated amine acquired by the step (1) (hereinafter referred to as a "second step" for easy explanation); and (3) measuring an amount of hydrogen peroxide generated in the step (2) or an amount of oxygen consumed in the step (2) (hereinafter referred to as a "third step" for easy explanation).

A concrete method of the present embodiment is an enzyme method. The enzyme method includes the following steps of: fractionating the glycosylated protein present in the sample into glycosylated amino acids or glycosylated peptides by use of an enzyme such as a protease (first step); adding FAOD to the glycosylated amino acids or the glycosylated peptides thereby producing hydrogen peroxide by oxidation-reduction reaction (second step); adding, to the sample, a peroxidase (POD) and a reducing agent that develops a color by oxidation so that the POD serving as a catalyst causes oxidation-reduction reaction between the hydrogen peroxide and the reducing agent (third step); and measuring color intensity of the reducing agent that has developed a color by the oxidation-reduction reaction thereby allowing the amount of the hydrogen peroxide to be measured (third step).

The following describes the above-described steps.

(5-1) First Step

In the first step, the glycosylated protein present in the sample is dissolved, and the glycosylated amine derived from the glycosylated protein present in the sample is adjusted.

The "glycosylated protein" means a (glycosylated) protein in which a sugar is bonded to a part of amino-acid residues or all amino-acid residues comprising a protein. The glycosylated protein is not particularly limited. An Example of the glycosylated protein is a protein such as HbA1c in which α-amino group of an amino terminal of an amino acid included in a protein is glycosylated. The HbA1c is used as an indicator for clinical diagnosis such as diagnosis of diabetes. The glycosylated protein may also be a protein complex in which the glycosylated protein is bonded to any other substance.

The protease is not particularly limited as long as the protease can dissolve the glycosylated protein present in the sample into the glycosylated amino acids or the glycosylated peptides. For example, a protease used for clinical examination is preferably employed.

Further, the "sample" is not particularly limited as long as the sample is an object to be examined as to a concentration of the glycosylated protein and whether or not the sample includes the glycosylated protein. Examples of the sample encompass biogenic samples such as: whole blood; plasma; serum; hemocyte; urine; and spinal fluid (that is, samples collected from an organism), a beverage such as juice, and foods such as soy sauce and sauce. Particularly, the whole blood and the hemocyte are employed as effective samples because the method of the present invention is applicable to the diagnosis of diabetes. In a case where glycosylated hemoglobin present in a red blood cell is measured, a sample for measuring the glycosylated hemoglobin is obtained by hemolyzing the whole blood itself or hemolyzing a red blood cell isolated from the whole blood though the method for obtaining the sample is not particularly limited.

A concrete condition under which the sample is reacted with the protease is not particularly limited as long as a desirable glycosylated amine is adjusted. A preferable condition may be taken as appropriate according to a concentration and a type of the sample, and a type and a concentration of the protease.

The concentration of the protease suitably employed for the measurement method of the present invention ranges, for example, from 0.1 U/ml to 1 MU/ml (preferably, from 1 U/ml to 500 KU/ml, more preferably, 5 U/ml to 100 KU/ml). However, the concentration of the protease is not limited to the above concentration. The concentration of the protease can be suitably determined according to a reaction condition, a type and a state of the sample, an ability of an experimenter, a reagent used by the experimenter, and the like.

Further, examples of the "glycosylated amine" encompass the glycosylated amino acids or the glycosylated peptides derived from the glycosylated protein included in the sample. A length of the glycosylated peptides is not particularly limited. An example of the length is a length which allows the protein of the present invention to act, for example, a length of 2 through 6 amino acid residues.

(5-2) Second Step

In the second step, the protein of the present invention is caused to act on the glycosylated amine derived from the glycosylated protein included in the sample, the glycosylated amine having been attained by the first step.

The fructosyl valyl histidine oxidase activity that the protein of the present invention has is not particularly limited. However, the greater fructosyl valyl histidine oxidase activity the protein of the present invention has makes it possible to detect the glycosylated amine at higher sensitivity. It is thereby possible to reduce in the usage of a fructosyl valyl histidine oxidase protein. Accordingly, it is preferable that the protein of the present invention has the great fructosyl valyl histidine oxidase activity.

A concentration of the fructosyl valyl histidine oxidase protein suitably employed for the measurement method of the present invention ranges, for example, from 0.1 U/ml to 500 U/ml (preferably, from 0.5 U/ml to 200 U/ml, more preferably, from 1.0 U/ml to 100 U/ml). However, the concentration of the fructosyl valyl histidine oxidase is not particularly limited. The concentration can be determined as appropriate according to the reaction condition, the type and the state of the sample, the ability of the experimenter, the reagent used by the experimenter, and the like.

Here, a definition of one unit (U) is identical to that described in the following "activity measurement method" in Examples.

In this step, the protein of the present invention is caused to act on the glycosylated amine. This action causes oxidative hydrolysis reaction thereby leading to consumption of oxygen. As a result, hydrogen peroxide is generated.

(5-3) Third Step

In the third step, the amount of hydrogen peroxide generated in the second step or the amount of oxygen consumed in the second step is measured. A concrete measurement method is not particularly limited as long as the amount of the generated hydrogen peroxide or the amount of the consumed oxygen is measured in the third step. Therefore, a conventional method can be employed as appropriate.

As described above, the method employed in the third step is not limited. An example of the method is an enzyme method. The enzyme method is conducted as follows. First, the glycosylated protein included in the sample is fractionated into the glycosylated amino acids or the glycosylated peptides by use of the enzyme such as the protease. Subsequently, a fructosyl valyl histidine oxidase is added to the glycosylated amino acids and/or the glycosylated peptides thereby causing oxidation-reduction reaction that leads to generation of hydrogen peroxide. Thereafter, the peroxidase (hereinafter referred to as a POD) and the reducing agent that develops a color by oxidation are added to the sample so that the POD serving as a catalyst causes oxidation-reduction reaction between the hydrogen peroxide and the reducing agent. The oxidation-reduction reaction causes the reducing agent to develop a color. The color intensity is measured thereby allowing the amount of the hydrogen peroxide to be measured.

A preferable POD employed in the third step is derived from a western green horseradish, a microbe or the like. Further, a concentration of the POD preferably ranges from 0.01 U/mL to 100 U/mL.

Examples of the preferable method for measuring the hydrogen peroxide in the third step encompass: a method for generating a pigment by oxidative condensation reaction of a phenolic, aniline or toluidine hydrogen donor (that is, a Trinder reagent) with a coupler (4-aminoantipyrine (4-AA), 3-methyl-2-benzothiazolinone hydrazone (MBTH) or the like) in the presence of the POD; and a method for using a leuco pigment that directly develops a color by oxidation in the presence of the POD. These methods are well-known to a person skilled in the art, and therefore can be generally and easily employed.

The Trinder reagent is not limited. For example, phenol and a derivative thereof can be suitably employed.

Examples of the coupler suitably employed in the third step encompass 4-aminoantipyrine, an aminoantipyrine derivative, vanilline diamine sulfonic acid, methyl benzothiazolinone hydrazone (MBTH) (more concretely, 3-methyl-2-benzothiazolinone hydrazone) and sulfonated methyl benzothiazolinone hydrazone (SMBTH) (more concretely, sulfonated 3-methyl-2-benzothiazolinone hydrazone).

The leuco pigment suitably employed in the third step is not limited. For example, a triphenylmethane derivative, a phenothiazine derivative or a diphenylamine derivative can be employed.

Other than the method for developing a color with use of the POD or the like, a measurement method employing various sensors is generally known to a person skilled in the art as the method for measuring the amount of hydrogen peroxide in the third step (the measurement method employing various sensors is not limited. See, for example, Japanese Patent Application Publication Toukai No. 2001-204494). Examples of electrodes used for the various sensors encompass an oxygen electrode, a carbon electrode, a gold electrode and a platinum electrode. The measurement method employing various sensors is conducted in the present invention as follows. An electrode serving as a working electrode to which an enzyme is immobilized, a counter electrode such as a platinum electrode, and a reference electrode such as an Ag/Cl electrode are all put in a buffer solution under a condition suitable for the present invention while the buffer solution is maintained at a constant temperature. Subsequently, a constant voltage is applied to the working electrode, and then a sample is added to the buffer solution. This causes enzyme reaction thereby leading to generation of hydrogen peroxide. In this manner, a value of current increased due to the generation of the hydrogen peroxide is measured.

Further, the amount of the hydrogen peroxide may be measured by an amperometric method employing the carbon electrode, the gold electrode, the platinum electrode and like electrodes. The amperometric method includes a method employing an immobilized electron mediator. The method employing the immobilized electron mediator is conducted as follows. An electrode serving as a working electrode to which an enzyme and an electron mediator (for example, potassium ferricyanide, ferrocene, an osmium derivative or phenazine methosulfate) are absorbed or to which a macromolecular matrix is immobilized by coralent binding, the counter electrode such as the platinum electrode, and the reference electrode such as an Ag/AgCl electrode are all put in the buffer solution under the condition suitable for the present invention while the buffer solution is maintained at a constant temperature. Subsequently, a constant voltage is applied to the working electrode, and then a sample is added to the buffer solution. This causes enzyme reaction thereby leading to generation of hydrogen peroxide. In this manner, a value of current increased due to the generation of hydrogen peroxide is measured.

As described above, it is also possible to measure the amount of glycosylated amine by measurement of the amount of oxygen consumed in the third step (the method for measuring the amount of consumed oxygen is not limited. See, for example, Japanese Patent Application Publication Tokukai No. 2001-204494). Concretely, the method for measuring the amount of consumed oxygen is conducted as follows. An oxygen electrode on which surface an enzyme is immobilized is put in the buffer solution under the condition suitable for the present invention while the buffer solution is maintained at a constant temperature. Subsequently, a sample is added to the buffer solution. In this manner, a value of reduced current is measured.

The amount of consumed oxygen may be measured by the amperometric method employing the carbon electrode, the gold electrode, the platinum electrode and like electrodes. According to the amperometric method, the value of increased current is measured by use of the electrode serving as a working electrode to which the enzyme and the mediator are immobilized, the counter electrode such as the platinum electrode, and the reference electrode such as the Ag/AgCl electrode. As described above, the value of increased current is measured. Here, examples of the mediator encompass potassium ferricyanide, ferrocene, an osmium derivative and phenazine methosulfate.

Further, an inactive protein may be added to a system (for example, a reaction solution) of steps of the measurement method of the present invention, in order to enhance stability of the protein of the present invention. The inactive protein is preferably serum albumin, globulin or fiber protein, more preferably, bovine serum albumin. A concentration of bovine serum albumin preferably ranges from 0.05% wt/vol to 1% wt/vol. The inactive protein also preferably includes no protease impurity that causes enzymolysis A concentration of fructosyl valyl histidine is measured from a specific volume of a sample and a specific volume of a reagent. Further, absorbance of fructosyl valyl histidine is measured as quickly as possible after mixing the sample with the reagent and prior to occurrence of effective change in the absorbance caused by fructosyl valyl histidine, in order to measure a sample blank. Concretely, it is appropriate to measure the first absorbance in 0.5 through 5 seconds after mixing the sample with the reagent. The second absorbance is generally measured at 37° C. in 3 through 5 minutes after the absorbance becomes steady under a condition where fructosyl valyl histidine has a concentration of 1 mg/dL. The reagent is generally standardized as an aqueous or serum solution having a known concentration of fructosyl valyl histidine.

6. Kit for Measuring Glycosylated Protein of the Present Invention

The kit for measuring the glycosylated protein of the present invention (hereinafter referred to as a "kit of the present invention") is characterized in including at least the protein (or the fructosyl valyl histidine oxidase agent) of the present invention.

The kit of the present invention may be a kit for measuring glycosylated hemoglobin. A state of the protein (or the fructosyl valyl histidine oxidase agent) of the present invention included in the kit of the present invention is not particularly limited. Examples of the state encompass an aqueous solution, a suspension and freeze-dried power. The freeze-dried power is manufactured by a conventional method.

The kit of the present invention may include various additives. A method for adding the additives is not particularly limited. Examples of the method for adding the additives encompass a method for adding an additive to a buffer including the protein of the present invention, a method for adding the protein of the present invention to a buffer including an additive, a method for simultaneously adding the protein of the present invention and a stabilizing agent to a buffer, and like methods.

The kit of the present invention may comprise at least the protein of the present invention (or the fructosyl valyl histidine oxidase agent), a peroxidase, and a reagent composite including a chromogen.

According to the measurement method of the present invention, hydrogen peroxide caused by oxidation of fructosyl valyl histidine is detected by means of peroxidase reaction. Therefore, the peroxidase and the chromogen (a reagent that develops a color in reaction to hydrogen peroxide) are preferably employed as the reagent composite. Compositions of the peroxidase and the chromogen (the reagent that develops a color in reaction to hydrogen peroxide) are not limited at all.

The chromogen (the reagent that develops a color in reaction to hydrogen peroxide) of the present invention is preferably stable in a solution and hard to be interfered by a bilirubin. One Example of the chromogen (the reagent that develops a color in reaction to hydrogen peroxide) suitable for the present invention is a reagent comprising a combination of a compound selected from 4-aminoantipyrine and 3-methyl-2-benzothiazolinone hydrazone (MBTH) with a compound selected from phenol, a phenol derivative, aniline and an aniline derivative. The chromogen (the reagent that develops a color in reaction to hydrogen peroxide) of the present invention may also be benzidine, a leuco pigment, 4-aminoantipyrine, phenol, naphhtol or an aniline derivative.

Further, the peroxidase suitable for the present invention is preferably a peroxidase derived from a Western green horseradish. A high-purity and low-cost peroxidase is commercially available as the peroxidase of the present invention. An enzyme concentration of the peroxidase should be great enough for quick and complete reaction, and therefore preferably ranges from 1,000 U/L to 50,000 U/L.

Furthermore, the reagent composite may include the buffer (for example, the borate buffer, the phosphate buffer, the Tris buffer or the GOOD buffer), in addition to the above-described components. The reagent composite may also include the chelating reagent (for example, the EDTA or O-dianisidine) that catches an ion that interferes with enzyme reaction, an ascorbic acid oxidase that scanvenges an ascorbic acid that is a substrate which interferes with quantitative determination of hydrogen peroxide, the surface-active agent (for example, the Triton X-100 or a NP-40), an antimicrobial agent and preservatives (for example, a streptomycin or a sodium azide). These reagents each may comprise a single reagent, or 2 or more reagents combined with each other.

The above-described buffer is not particularly limited. It is possible to employ a buffer having an efficient buffer performance at pH ranging from 6 to 8.5. Examples of the buffer having such pH encompass phosphoric acid, Tris, bis-trispropane, N-tris(hydroxymethyl)methyl-2-aminoethanesulfonic acid (TES), 2-morpholinoethanesulfonic acid monohydrate (MES), piperazine-1,4-bis(2-ethanesulfonic acid) (PIPES), 2-[4-(2-Hydroxyethyl)-1-piperazinyl]ethanesulfonic acid) (HEPES), and 3-[N-tris(hydroxymethyl)methylamino]-2-hydroxypropanesulfonic acid (TAPSO). Particularly, the MES and the PIPES are preferable buffers. Further, a concentration of the buffer preferably ranges from 20 mM to 200 mM, and pH of the buffer preferably ranges from 6 to 7.

The kit of the present invention may include the fructosyl valyl histidine oxidase, the buffer, the protease, the POD, the chromogenic reagent, the chelating agent that catches the ion that interferes with enzyme reaction, the ascorbic acid oxidase that scanvenges ascorbic acid that is the substrate which interferes with quantitative determination of hydrogen peroxide, the surface-active agent, the stabilizing agent, a diluting agent, the antimicrobial agent, the preservatives, a well plate, a fluorescent scanner, an autoanalyzer, an instruction manual made up of a recording medium such as a paper on which the measurement method of the present invention is described, and the like.

The measurement kit of the present invention can be used for the method for measuring the glycosylated protein of the present invention and measurement of the fructosyl amino acid, particularly for measurement of the glycosylated hemoglobin.

7. Sensor for Measuring Glycosylated Protein of the Present Invention

The sensor for measuring the glycosylated protein of the present invention (hereinafter referred to as a "sensor of the present invention") is a sensor for detecting the glycosylated protein, and includes at least the protein (or the fructosyl valyl histidine oxidase agent) of the present invention.

The sensor of the present invention is used for the measurement method of the present invention. The sensor of the present invention is used particularly for the measurement of the glycosylated hemoglobin. Therefore, the sensor of the present invention may comprise components used for the measurement method of the present invention. It is therefore possible to employ, as description of the components, the descriptions of the buffer and the like described in sections describing the measurement method and the kit of the present invention.

The sensor of an embodiment of the present invention is a sensor to which support the protein (or the fructosyl valyl histidine oxidase agent) of the present invention is immobilized. The support is not particularly limited as long as the protein (or the fructosyl valyl histidine oxidase agent) of the present invention is immobilized to the support. A support having a shape and material suitable for properties of the protein of the present invention may be employed. The shape of the support is not particularly limited as long as the support has an area enough to immobilize the protein (or the fructosyl valyl histidine oxidase agent) of the present invention. Examples of the shape of the support encompass a substrate, a bead and a filter. Further, examples of the material of the support encompass an inorganic material, a natural polymer and a synthetic polymer.

The present invention is not limited to the description of the embodiments above, but may be altered by a skilled person within the scope of the claims. An embodiment based on a proper combination of technical means disclosed in different embodiments is encompassed in the technical scope of the present invention.

EXAMPLE

The following more specifically describes the present invention via Examples.

1. Activity Measuring Reagent

Table 1 shows a composition of an activity measuring reagent used in the present example. The chemical compounds used in the present examples were purchased from NACALAI TESQUE, INC. unless otherwise particularly stated.

TABLE 1

| Activity measuring reagent | |
| --- | --- |
| Western green horseradish peroxidase | 5000 U/L |
| Substrate (F-K, F-V, or F-VH) | 2 mM |
| 4-aminoantipyrine | 0.01% (W/V) |
| Phenol | 0.02% (W/V) |
| MES (pH 6.5) | 50 mM |

The following describes an activity measurement condition of the fructosyl valyl histidine oxidase of the present example.

2. Activity Measurement Method

The following describes an activity measurement method of the following examples 1 through 3.

An enzyme activity to a substrate was measured by an increase in absorbance of a pigment as a result of peroxidase reaction involving hydrogen peroxide generated by enzyme reaction. First, 3 ml of activity measuring reagent was heated at 37° C. for 5 minutes, and then 0.1 ml of enzyme solution diluted in advance by an enzyme diluent (a 50 mM potassium phosphate buffer (pH 7.5)) was added to the activity measuring reagent, thereby starting the reaction.

The reaction was conducted at 37° C. for 5 minutes, and then a change in the absorbance at 500 nm ($\Delta OD_{test}$/min) was measured. Meanwhile, a blank test was conducted by adding, instead of the enzyme solution, 0.1 ml of enzyme diluent to the activity measuring reagent, and then measuring a change in the absorbance at 500 nm ($\Delta OD_{blank}$/min) in the same way. The enzyme activity was calculated from the changes in absorbance on the basis of the following formula, and is described by unit (U) where an amount of enzyme that oxidizes 1 micromole of substrate in one minute under the above-described condition is 1 unit (U).

—Formula—

Activity value(U/ml)={$\Delta$OD/min($\Delta$ODtest−$\Delta$OD-blank)×3.1(ml)×dilution magnification}/{13×1.0 (cm)×0.1(ml)}. In the above formula, "3.1 (ml)" is the whole liquid quantity;
"13" is a millimolar absorbance index;
"1.0 (cm)" is an optical length of a cell; and
"0.1 (ml)" is the enzyme sample quantity.

3. Example 1

Cloning of Fructosyl Valyl Histidine Oxidase Gene

A genome database (http://www.ncbi.nlm.nih.gov/sutils/genom_table.cgi?organism=fungi&database=321614) of *Phaeosphaeria nodorum* was searched in order to conduct cDNA cloning of the fructosyl valyl histidine oxidase derived from *Phaeosphaeria nodorum*.

From the genome database, genes that possibly encoded for a FAD-dependent oxidoreductase were extracted. Among the genes extracted by the above search, genes that possibly encoded for an enzyme that substantially acted on fructosyl valine were further selected. As a result, genes ranging from 75,143 bp to 76,625 bp of GenBank no. AAGI01000177 239512 bp *Phaeosphaeria nodorum* SN15 cont1.177, whole genome shotgun Sequence (http://www.ncbi.nlm.nih.gov/entrez/viewer.fcgi?tool=portal&db=nuccore&term=&query%5Fkey=11&dopt=gb&dispmax=20&page=1&qty=1&WebEnv=0x3fThZQ1ubv2E4QUtcTFz S2yHOV3ljOuR6kUwGyNOVEiqCGdFac8yYAlfzZG%2DvpBxXqNrPNESW3skk%402644558678701720%5F0135SID&WebEnvRq=1) were selected as a cloning candidate gene.

Thereafter, an entire sequence of the cDNA of the cloning candidate gene which entire sequence encodes for the protein of the present invention was deduced by using a tool (http://www.fruitfly.org/seq_tools/splice.html) for predicting a splicing site (exon and intron) and comparing the cDNA with a known fructosyl amino acid oxidase gene of another organism. On the basis of the deduction, the entire sequence of the cDNA was synthesized by a conventional method. The conventional method is a method for synthesizing the entire sequence of the cDNA by synthesizing all gene fragments by PCR, that is, by preparing a total RNA, extracting an mRNA and then reversetranscribing the mRNA. Subsequently, a terminal of the cDNA was turned to a blunt end by use of a Blunting high manufactured by TOYOBO Co., Ltd., and then the cDNA was subcloned to a SmaI site of pUC118. Thereafter, the sequence of the cDNA was analyzed to find the nucleotide sequence shown in SEQ ID NO: 2. In the nucleotide sequence shown in SEQ ID NO: 2, a region for encoding is from the first nucleotide to 1314$^{th}$ nucleotide. A start codon of the nucleotide sequence shown in SEQ ID NO: 2 is from the first nucleotide to the third nucleotide. A stop codon TAG of the nucleotide sequence shown in SEQ ID NO: 2 is from 1312th nucleotide to 1314$^{th}$ nucleotide. The amino acid sequence found from the nucleotide sequence shown in SEQ ID NO: 2 was shown in SEQ ID NO: 1.

The attained cDNA was a DNA that encodes for a novel fructosyl valyl histidine oxidase, as described in the following Examples 2 and 3.

4. Example 2

Mass Expression of Fructosyl Valyl Histidine Oxidase Gene in *Escherichia coli*, Purification and Enzyme Assay of the Fructosyl Valyl Histidine Oxidase Gene In Example 2, a plasmid including the fructosyl valyl histidine oxidase gene having the nucleotide sequence shown in SEQ ID NO: 2 was produced, and a mass expression of fructosyl valyl histidine oxidase protein in *Escherichia coli* was attempted.

First, an entire cDNA region (the first nucleotide through 1311$^{th}$ nucleotide of the nucleotide sequence shown in SEQ ID NO: 2) other than a stop codon of the fructosyl valyl histidine oxidase gene was amplified by PCR. In the amplification, an NdeI cleavage site was inserted at an N terminal of an amino acid sequence by use of a primer P1 (5'-GGAAT-TCCATATGGCGCCCTCCAGAGCAAACAC-CAGTGTCATT-3' wherein "CATATG" of this nucleotide sequence is the NdeI site) shown in SEQ ID NO: 3. Further, the XhoI cleavage site was inserted at a C terminal of the amino acid sequence by used of a primer P2 (5'-CCGCTC-GAGCAAGTTCGCCCTCGGCTTATCAT-GATTCCAACC-3' wherein "CTCGAG" of this sequence is the XhoI site) shown in SEQ ID NO: 4. Subsequently, the DNA fragment was subcloned to an NdeI-XhoI site of a pET-23b vector (Novagen) in a direction of a T7 promoter. Thereby, a plasmid was produced, and the plasmid was named pIE353 as a plasmid that expresses the fructosyl valyl histidine oxidase.

Subsequently, the *Escherichia coli* BL21 CodonPlus (DE3)-RIL (Stratagene) was transformed by use of the plasmid pIE353, and then a transformant BL21 CodonPlus (DE3)-RIL (pIE353) having an ampicillin resistance was selected.

Thereafter, the transformant was cultured in a culture medium. The culture medium for culturing the transformant was prepared as follows. 200 ml of TB culture medium was dispensed into a 2 liter of Sakaguchi flask, and autoclaved at 121° C. for 20 minutes. The culture medium was cooled, and then an aseptically-filtrated ampicillin was added to the culture medium to a final concentration of 100 µg/ml. The culture medium was inoculated with 2 ml of culture solution of BL21 CodonPlus (DE3)-RIL (pIE353) that has been cultured in an LB culture medium including 100 µg/ml of ampicillin at 30° C. for 16 hours in advance.

Subsequently, the transformant was incubated in the culture medium aerobically with stirring at 30° C. for 24 hours. After the incubation of transformant, the bacteria included in the culture medium were collected by means of centrifugal separation. Thereafter, the bacteria were suspended in a 50 mM potassium phosphate buffer (pH 7.5), and then disrupted by ultrasonic waves.

Subsequently, the suspension was centrifuged so as to attain supernatant fluid thereof serving as a crude enzyme solution. A fructosyl valyl histidine oxidase activity in the crude enzyme solution was measured by use of an enzyme activity measuring reagent including fructosyl valyl histidine as a substrate. The fructosyl valyl histidine oxidase activity was approximately 1.0 U/ml. The crude enzyme solution was purified according to a specific protocol by use of a MagExtractor-His-tag—manufactured by TOYOBO Co., Ltd. As a result, a purified enzyme sample (IE353) was produced. The IE353 sample produced by the above method was found to be an enzyme comprising a single enzyme, by SDS-polyacrylamide gel electrophoresis.

An enzyme activity of the IE353 sample was measured by use of the enzyme activity measuring reagent including fructosyl valyl histidine as a substrate. As a result, it was found that the IE353 sample had the fructosyl valyl histidine oxidase activity.

5. Example 3

Property Evaluation of Fructosyl Valyl Histidine Oxidase Protein

Table 2 shows measurement results of the fructosyl valyl histidine oxidase (IE353) of the present invention, conventional enzymes FPOX-CE and FPOX-EE manufactured by KIKKOMAM Corporation, in terms of a thermal stability, a substrate specificity, and a Km value to fructosyl valyl histidine (F-VH).

The thermal stability was worked out as follows. First, solutions of the fructosyl valyl histidine oxidase (IE353), the conventional enzymes FPOX-CE and FPOX-EE were respectively prepared at a concentration of 0.1 mg/mL with the 50 mM potassium phosphate buffer (pH 7.5), and heated at 50° C. for 10 minutes. Thereafter, the thermal stability was calculated by the following expression.

Thermal stability(%)=(activity value after heating at 50° C. for 10 minutes)÷(activity value without heating)×100

Further, the substrate specificity was worked out as follows. First, solutions of substrates of the fructosyl valyl histidine oxidase (IE353), the conventional enzymes FPOX-CE and FPOX-EE were respectively prepared to have a concentration of 10 mM. Subsequently, activity values thereof were measured by the above-described activity measurement method. On the basis of the measured activity values, the substrate specificity was calculated by the following expression. Note that F-K in the expression indicates fructosyl lysine serving as a substrate for enzyme reaction. The smaller a value of the substrate specificity calculated by the expression is, the more excellent the substrate specificity to F-VH is. Thus, a smaller activity value is more preferable.

Substrate specificity(F-K/F-VH)=(activity value in a case where F-K is a substrate)÷(activity value in a case where F-VH is a substrate)

The Km value to F-VH was worked out as follows. Samples of F-VH concentrations of 1.75 mM, 0.88 mM, 0.58 mM, 0.35 mM, 0.25 mM and 0.18 mM were prepared respectively. Subsequently, activities in the samples were measured by the above-described activity measurement method. On the basis of the measured activities, the Km value of F-VH was calculated by means of Lineweaver-Burk plot.

TABLE 2

| | Enzyme | | |
|---|---|---|---|
| | IE353 | FPOX-CE | FPOX-EE |
| | | Origin | |
| | P. nodurum | Coniochaeta sp. | E. terrenum |
| Thermal stability (50° C., 10 min) | 76% | 0% | 0% |
| Substrate specificity: | | | |
| F-K/F-VH | 0.24 | 0.41 | 0.11 |
| Km (mM) F-VH | 0.5 | 1.0 | 1.0 |

As is clear from Table 2, the IE353 has more excellent thermal stability and substrate specificity, and a lower Km value than those of the FPOX-CE and the FPOX-EE. The lower Km value means an excellent affinity to a substance, that is, even a low substrate concentration causes an excellent reactivity. It is therefore possible to reduce the amount of the fructosyl valyl histidine oxidase to be added to a reagent for measuring a glycosylated protein.

6. Activity Measurement Method

The following describes an activity measurement method of FAOD of Examples 4 through 7 and reference example 1.

An enzyme activity of FAOD to a substrate was measured by an increase in absorbance of a pigment as a result of peroxidase reaction involving hydrogen peroxide generated by enzyme reaction.

First, 3 ml of activity measuring reagent was heated at 37° C. for 5 minutes, and then 0.1 ml of enzyme solution diluted in advance by an enzyme diluent (a 50 mM potassium phosphate buffer (pH 6.5) including 0.1% of Triton X-100) was added to the activity measuring reagent, thereby starting the reaction.

The reaction was conducted at 37° C. for 5 minutes, and then a change in the absorbance at 500 nm per unit of time ($\Delta OD_{test}$/min) was measured. Meanwhile, a blank test was conducted by adding, instead of the enzyme solution, 0.1 ml of enzyme diluent to the activity measuring reagent, and then measuring a change in the absorbance at 500 nm ($\Delta OD_{blank}$/min), as with the above-described measurement.

An enzyme activity was calculated from the changes in the absorbance on the basis of the following formula, and is described by unit (U) where an amount of enzyme that oxidizes 1 micromole of substrate in one minute under the above-described condition is 1 unit (U).

—Formula—

Activity value(U/ml)={(($\Delta OD$test/min)−($\Delta OD$blank/min))×3.1(ml)×dilution magnification}/(13×1.0 (cm)×0.1(ml)).

In the above formula, "3.1 (ml)" is the whole liquid quantity, "13" is a millimolar absorbance index, "1.0 (cm)" is an optical length of a cell, and "0.1 (ml)" is the enzyme sample quantity.

7. Substrate Specificity Evaluation Method

The following describes a substrate specificity evaluation method of FAOD of Examples 4 through 7 and reference example 1.

The activity measuring reagents were prepared such that the respective substrates (F-K: fructosyl lysine, F-V: fructosyl valine, and F-VH: fructosyl valyl histidine) have a concentration of 2 mM, and then an activity value ratio (substrate specificity) was worked out by the following formulas and the above-described activity measurement method.

(F-V/F-VH)=(activity value in a case where F-V is a substrate)÷(activity value in a case where F-VH is a substrate)

(F-K/F-VH)=(activity value in a case where F-K is a substrate)÷(activity value in a case where F-VH is a substrate)

Here, the smaller the activity value ratio calculated by the above formulas is, the more excellent the substrate specificity to F-VH is. Thus, a smaller activity value is more preferable.

8. Thermal Stability Evaluation Method

The following describes a thermal stability evaluation method of FAOD of Examples 4 through 7 and reference example 1.

First, a purified enzyme sample was solved in a 50 mM potassium phosphate buffer (pH 6.5) to have a concentration of 0.1 mg/mL, and then the 50 mM potassium phosphate buffer was heated at 50° C. for 10 minutes. Note that in a case of a triple mutant protein described later, a heat temperature was 55° C. In this manner, the thermal stability (%) of the purified enzyme sample was calculated by the following formula.

Thermal stability(%)={(activity value after heating at 50° C. for 10 minutes)/(activity value prior to heating)}×100

Example 4

Modification of Fructosyl Valyl Histidine Oxidase Gene and Protein

First, a primer R1 and a primer R2 were synthesized in order to randomly replace, with another amino acid, isoleucine at 58th position of the amino acid sequence shown in SEQ ID NO: 1.

```
Primer R1:
                                    (SEQ ID NO: 5)
5'-cttattgaggtcattgcctgcagattgcgatgaagg-3'

Primer R2:
                                    (SEQ ID NO: 6)
5'-nnsatgggcgttagcttgcgaaacccagtggac-3'
```

Subsequently, a recombinant plasmid in which mutation was introduced into the isoleucine at 58$^{th}$ position of the amino acid sequence shown in SEQ ID NO: 1 was produced by use of the pIE353, the primer R1, the primer R2 and a KOD-Plus Site-Directed Mutagenesis Kit (manufactured by TOYOBO Co., Ltd.). Thereafter, a BL21 CodonPlus (DE3)-RIL was transformed by use of the recombinant plasmid, and then 100 colonies having an ampicillin resistance were selected. Subsequently, nucleotide sequences of 100 recombinant plasmids in the 100 colonies were examined. As a result of the examination, plasmids in which the isoleucine at 58$^{th}$ position of the amino acid sequence shown in SEQ ID NO: 1 was replaced with 19 types of amino acids, respectively, were successfully acquired.

Specifically, a plasmid (pIE353-I58T) in which a nucleotide sequence (att) that encodes for 58$^{th}$ position of the amino acid sequence shown in SEQ ID NO: 1 was replaced with a nucleotide sequence (acc) that encodes for threonine (T) was successfully acquired. A purified enzyme sample made from the plasmid is referred to as IE353-I58T.

Further, a plasmid (pIE353-I58A) in which the nucleotide sequence (att) that encodes for 58$^{th}$ position of the amino acid sequence shown in SEQ ID NO: 1 was replaced with a nucleotide sequence (gct) that encodes for alanine (A) was successfully acquired. A purified enzyme sample made from the plasmid is referred to as IE353-I58A.

Further, a plasmid (pIE353-I58V) in which the nucleotide sequence (att) that encodes for 58$^{th}$ position of the amino acid sequence shown in SEQ ID NO: 1 was replaced with a nucleotide sequence (gtc) that encodes for valine (V) was successfully acquired. A purified enzyme sample made from the plasmid is referred to as IE353-I58V.

Further, a plasmid (pIE353-I58L) in which the nucleotide sequence (att) that encodes for 58$^{th}$ position of the amino acid sequence shown in SEQ ID NO: 1 was replaced with a nucleotide sequence (ctc) that encodes for leucine (L) was successfully acquired. A purified enzyme sample made from the plasmid is referred to as IE353-I58L.

Further, a plasmid (pIE353-I58M) in which the nucleotide sequence (att) that encodes for 58$^{th}$ position of the amino acid sequence shown in SEQ ID NO: 1 was replaced with a nucleotide sequence (atg) that encodes for methionine (M) was successfully acquired. A purified enzyme sample made from the plasmid is referred to as IE353-I58M.

Further, a plasmid (pIE353-I58F) in which the nucleotide sequence (att) that encodes for 58$^{th}$ position of the amino acid sequence shown in SEQ ID NO: 1 was replaced with a nucleotide sequence (ttc) that encodes for phenylalanine (F) was successfully acquired. A purified enzyme sample made from the plasmid is referred to as IE353-I58F.

Further, a plasmid (pIE353-I58S) in which the nucleotide sequence (att) that encodes for 58$^{th}$ position of the amino acid sequence shown in SEQ ID NO: 1 was replaced with a nucleotide sequence (tcg) that encodes for serine (S) was successfully acquired. A purified enzyme sample made from the plasmid is referred to as IE353-I58S.

Further, a plasmid (pIE353-I58Q) in which the nucleotide sequence (att) that encodes for 58$^{th}$ position of the amino acid sequence shown in SEQ ID NO: 1 was replaced with a nucleotide sequence (caa) that encodes for glutamine (Q) was successfully acquired. A purified enzyme sample made from the plasmid is referred to as IE353-I58Q.

Further, a plasmid (pIE353-I58C) in which the nucleotide sequence (att) that encodes for 58$^{th}$ position of the amino acid sequence shown in SEQ ID NO: 1 was replaced with a nucleotide sequence (tgc) that encodes for cysteine (C) was successfully acquired. A purified enzyme sample made from the plasmid is referred to as IE353-I58C.

Further, a plasmid (pIE353-I58Y) in which the nucleotide sequence (att) that encodes for 58$^{th}$ position of the amino acid sequence shown in SEQ ID NO: 1 was replaced with a nucleotide sequence (tac) that encodes for tyrosine (Y) was successfully acquired. A purified enzyme sample made from the plasmid is referred to as IE353-I58Y.

Further, a plasmid (pIE353-I58N) in which the nucleotide sequence (att) that encodes for 58$^{th}$ position of the amino acid sequence shown in SEQ ID NO: 1 was replaced with a nucleotide sequence (aac) that encodes for asparagine (N) was successfully acquired. A purified enzyme sample made from the plasmid is referred to as IE353-I58N.

Further, a plasmid (pIE353-I58K) in which the nucleotide sequence (att) that encodes for 58$^{th}$ position of the amino acid sequence shown in SEQ ID NO: 1 was replaced with a nucleotide sequence (aag) that encodes for lysine (K) was successfully acquired. A purified enzyme sample made from the plasmid is referred to as IE353-I58K.

Further, a plasmid (pIE353-I58H) in which the nucleotide sequence (att) that encodes for 58$^{th}$ position of the amino acid sequence shown in SEQ ID NO: 1 was replaced with a nucleotide sequence (cac) that encodes for histidine (H) was successfully acquired. A purified enzyme sample made from the plasmid is referred to as IE353-I58H.

Further, a plasmid (pIE353-I58R) in which the nucleotide sequence (att) that encodes for 58$^{th}$ position of the amino acid sequence shown in SEQ ID NO: 1 was replaced with a nucleotide sequence (cgc) that encodes for arginine (R) was successfully acquired. A purified enzyme sample made from the plasmid is referred to as IE353-I58R.

Further, a plasmid (pIE353-I58D) in which the nucleotide sequence (att) that encodes for 58$^{th}$ position of the amino acid sequence shown in SEQ ID NO: 1 was replaced with a nucleotide sequence (gac) that encodes for asparagine acid (D) was successfully acquired. A purified enzyme sample made from the plasmid is referred to as IE353-I58D.

Further, a plasmid (pIE353-I58E) in which the nucleotide sequence (att) that encodes for 58$^{th}$ position of the amino acid sequence shown in SEQ ID NO: 1 was replaced with a nucleotide sequence (gaa) that encodes for glutamic acid (E) was successfully acquired. A purified enzyme sample made from the plasmid is referred to as IE353-I58E.

Further, a plasmid (pIE353-I58W) in which the nucleotide sequence (att) that encodes for 58$^{th}$ position of the amino acid sequence shown in SEQ ID NO: 1 was replaced with a nucleotide sequence (tgg) that encodes for tryptophan (W) was successfully acquired. A purified enzyme sample made from the plasmid is referred to as IE353-I58W.

Further, a plasmid (pIE353-I58P) in which the nucleotide sequence (att) that encodes for 58$^{th}$ position of the amino acid sequence shown in SEQ ID NO: 1 was replaced with a nucleotide sequence (ccc) that encodes for proline (P) was successfully acquired. A purified enzyme sample made from the plasmid is referred to as IE353-I58P.

Further, a plasmid (pIE353-I58G) in which the nucleotide sequence (att) that encodes for 58$^{th}$ position of the amino acid sequence shown in SEQ ID NO: 1 was replaced with a nucleotide sequence (gtt) that encodes for glycine (G) was successfully acquired. A purified enzyme sample made from the plasmid is referred to as IE353-I58G.

The BL21 CodonPlus (DE3)-RIL was transformed by use of each of the acquired plasmids, and then a transformant having an ampicillin resistance was selected.

As is the case with the above-described IE353, the selected transformant was cultured, and then a crude enzyme solution acquired by culturing the selected transformant was purified. As a result, purified enzyme samples (IE353-I58T, IE353-I58A, IE353-I58V, IE353-I58L, IE353-I58G, IE353-I58M, IE353-I58F, IE353-I58S, IE353-I58Q, IE353-I58C, IE353-I58Y, IE353-I58N, IE353-I58K, IE353-I58H, IE353-I58R, IE353-I58D, IE353-I58E, IE353-I58W and IE353-I58P) were acquired. The purified enzyme samples were analyzed by SDS-polyacrylamide gel electrophoresis. As a result of the analysis, it was confirmed that the purified enzyme samples each comprised a single protein.

10. Example 5

Property Evaluation of Fructosyl Valyl Histidine Oxidase Mutant Protein

According to the above-described activity measurement method, enzyme activities of a wild-type fructosyl valyl histidine oxidase (IE353) and the 19 types of purified enzyme samples (IE353-I58T, IE353-I58A, IE353-I58V, IE353-I58L, IE353-I58G, IE353-I58M, IE353-I58F, IE353-I58S, IE353-I58Q, IE353-I58C, IE353-I58Y, IE353-I58N, IE353-I58K, IE353-I58H, IE353-I58R, IE353-I58D, IE353-I58E, IE353-I58W, IE353-I58P) were measured.

Among the above purified enzyme samples, purified enzyme samples having a fructosyl valyl histidine oxidase activity were IE353, IE353-I58T, IE353-I58M, IE353-I58S, IE353-I58V, IE353-I58A, IE353-I58N and IE353-I58L.

Further, a substrate specificity and a thermal stability of the purified enzyme samples having the fructosyl valyl histidine oxidase activity were evaluated by the above-described substrate specificity evaluation method and thermal stability evaluation method. The result of the evaluation is shown in Table 3.

TABLE 3

| I58X | F-V/F-VH | F-K/F-VH | Thermal stability (%) [ratio] |
|---|---|---|---|
| — | 4.9 | 0.13 | 73.2 [1.00] |
| T | 0.5 | 0.03 | 56.5 [0.77] |

TABLE 3-continued

| I58X | F-V/F-VH | F-K/F-VH | Thermal stability (%) [ratio] |
|---|---|---|---|
| M | 1.0 | 0.11 | 101.4 [1.39] |
| S | 1.1 | 0.04 | 81.6 [1.11] |
| V | 1.5 | 0.03 | 69.0 [0.94] |
| A | 1.9 | 0.05 | 95.5 [1.30] |
| N | 2.5 | 0.10 | 11.4 [0.16] |
| L | 3.5 | 0.12 | 70.3 [0.96] |

The thermal stability (%) of the purified enzyme samples was also evaluated by comparison with the wild-type fructosyl valyl histidine oxidase. That is, it was put that the thermal stability of the wild-type fructosyl valyl histidine oxidase was 1.00, and a purified enzyme sample having a value larger than 1.00 was evaluated as a purified enzyme sample "having an improved thermal stability". This evaluation makes it possible to evaluate the thermal stability of the purified enzyme samples more objectively.

As shown in Table 3, it is apparent that a mutant protein in which the isoleucine at 58$^{th}$ position of the amino acid sequence shown in SEQ ID NO: 1 is replaced with another amino acid (T, M, S, V, A, N or L) has smaller F-K/F-VH and F-V/F-VH than those of the wild-type fructosyl valyl histidine oxidase protein, that is, the mutant protein has more improved substrate specificity than that of the wild-type fructosyl valyl histidine oxidase protein. Further, it is apparent that the mutant protein in which the isoleucine at 58$^{th}$ position is replaced with methionine (M), alanine (A) or serine (S) has more improved thermal stability than that of the wild-type fructosyl valyl histidine oxidase protein.

11. Example 6

Fructosyl Valyl Histidine Oxidase Mutant Protein (Double Mutant Protein) in which an Amino Acid is Further Replaced with Another Amino Acid, and Property Evaluation of the Mutant Protein The following describes how a property of a mutant protein changed in a case where in the mutant protein, an amino acid other than the isoleucine at 58$^{th}$ position of the amino acid sequence shown in SEQ ID NO: 1 was also replaced with another amino acid in addition to replacement of the isoleucine.

First, an expression plasmid of a mutant protein in which phenylalanine at 282$^{th}$ position of the amino acid sequence shown in SEQ ID NO: 1 was replaced with tyrosine was produced. The following describes a method for producing the expression plasmid.

First, a primer Y1 and a primer Y2 were synthesized in order to replace, with tyrosine, the phenylalanine at 282$^{th}$ position of the amino acid sequence shown in SEQ ID NO: 1.

```
Primer Y1:
                                            (SEQ ID NO: 7)
5'-tatacgcgcttcaagatgcatcaaccctttggcg-3'

Primer Y2:
                                            (SEQ ID NO: 8)
5'-gccaggaaactcgtcgcagactttgatcacg-3'
```

Subsequently, a recombinant plasmid in which the phenylalanine at 282$^{th}$ position was replaced with tyrosine was produced by use of the pIE353, the primer Y1, the primer Y2 and the KOD-Plus Site-Directed Mutagenesis Kit (manufactured by TOYOBO Co., Ltd.). Specifically, a recombinant plasmid (pIE353-F282Y) in which a nucleotide sequence (ttc) that encodes for the phenylalanine at 282$^{th}$ position of the amino acid sequence shown in SEQ ID NO: 1 was replaced with a nucleotide sequence (tat) that encodes for tyrosine (Y) was successfully acquired. As shown in Table 4, a purified enzyme sample (IE353-F282Y) made from the pIE353-F282Y has more improved thermal stability than that of the wild-type fructosyl valyl histidine oxidase.

Subsequently, an expression plasmid of a mutant protein in which the isoleucine at 58$^{th}$ position was replaced with another amino acid in addition to replacing, with tyrosine, the phenylalanine at 282$^{th}$ position was produced by use of the pIE353-F282Y, the primer R1, the primer R2 and the KOD-Plus Site-Directed Mutagenesis Kit (manufactured by TOYOBO Co., Ltd.). The method for producing the above expression plasmid is basically identical to the method for producing the expression plasmid of the mutant protein in which only the isoleucine at 58$^{th}$ position is replaced with another amino acid. Therefore, detailed description for the method for producing the above expression plasmid is omitted here.

Thereafter, purified enzyme samples were produced by use of the produced expression plasmid, by a method identical to the method by which the purified enzyme samples shown in Table 3 were produced. The substrate specificity and the thermal stability of these purified enzyme samples were evaluated. The result of the evaluation is shown in Table 4.

TABLE 4

| I58X (-F282Y) | F-V/F-VH | F-K/F-VH | Thermal stability (%) [ratio] |
|---|---|---|---|
| — | 4.4 | 0.11 | 87.5 [1.00] |
| T | 0.5 | 0.02 | 74.0 [0.85] |
| M | 1.0 | 0.11 | 98.0 [1.12] |
| S | 1.2 | 0.04 | 88.7 [1.01] |
| V | 1.5 | 0.03 | 86.0 [0.98] |
| A | 2.1 | 0.08 | 102.7 [1.17] |
| N | 2.7 | 0.08 | 44.7 [0.51] |
| L | 3.1 | 0.10 | 84.0 [0.96] |

As shown in Table 4, it is apparent that the mutant protein in which the isoleucine at 58$^{th}$ position of the amino acid sequence SEQ ID NO: 1 has been also replaced with another amino acid in the IE353-F282Y also has smaller F-K/F-VH and F-V/F-VH than those of an unmodified fructosyl valyl histidine oxidase protein (IE353-F282Y), that is, the mutant protein has more improved substrate specificity than that of the unmodified fructosyl valyl histidine oxidase protein.

Further, most of the purified enzyme samples had an excellent thermal stability. For example, a purified enzyme sample in which the isoleucine was replaced with M or A had drastically improved thermal stability compared to that of the wild-type fructosyl valyl histidine oxidase.

12. Example 7

Fructosyl Valyl Histidine Oxidase Mutant Protein (Triple Mutant Protein) in which an Amino Acid is Yet Further Replaced with Another Amino Acid, and Property Evaluation of the Mutant Protein The following describes how a property of a mutant protein changed in a case where in the mutant protein, an amino acid other than the isoleucine at 58$^{th}$ position and the phenylalanine at 282$^{th}$ position of the amino acid sequence shown in SEQ ID NO: 1 was also replaced with another amino acid in addition to replacement of the isoleucine and the phenylalanine.

First, an expression plasmid of a mutant protein in which not only the phenylalanine at 282$^{th}$ position of the amino acid sequence shown in SEQ ID NO: 1 was replaced with tyrosine but also the glycine at 110$^{th}$ position of the amino acid sequence shown in SEQ ID NO: 1 was replaced with glutamine was produced. The following describes a method for producing the expression plasmid.

First, a primer Q1 and a primer Q2 were synthesized in order to replace, with tyrosine, the phenylalanine at 282$^{th}$ position of the amino acid sequence shown in SEQ ID NO: 1.

```
Primer Q1:
                                     (SEQ ID NO: 9)
5'-taccaagctctcgtggacgcgggcttggat-3'

Primer Q2:
                                    (SEQ ID NO: 10)
5'-cagtaccaagctctcgtggacgcgggctt-3'
```

Thereafter, a recombinant plasmid in which not only the phenylalanine at 282$^{th}$ position was replaced with tyrosine but also the glycine at 110$^{th}$ position was replaced with glutamine was produced by use of the pIE353-F282Y, the primer Y1, the primer Y2 and the KOD-Plus Site-Directed Mutagenesis Kit (manufactured by TOYOBO Co., Ltd.). Specifically, the recombinant plasmid (pIE353-G110Q+F282Y) in which not only a nucleotide sequence (ttc) that encodes for the phenylalanine at 282$^{th}$ position of the amino acid sequence shown in SEQ ID NO: 1 was replaced with a nucleotide sequence (tat) that encodes for tyrosine (Y) but also a nucleotide sequence (gga) that encodes for the glycine at 110$^{th}$ position of the amino acid shown in SEQ ID NO: 1 was replaced with a nucleotide sequence (cag) that encodes for glutamine (Q) was successfully acquired.

Subsequently, an expression plasmid of a mutant protein in which the isoleucine at 58$^{th}$ position was also replaced with another amino acid in addition to replacing the phenylalanine at 282$^{th}$ position with tyrosine and replacing the glycine at 110$^{th}$ position with glutamine was produced by use of the pIE353-G110Q+F282Y, the primer R1, primer R2 and the KOD-Plus Site-Directed Mutagenesis Kit (manufactured by TOYOBO Co., Ltd.). The method for producing the above expression plasmid is basically identical to the method for producing the expression plasmid of the mutant protein in which only the isoleucine at 58$^{th}$ position is replaced with another amino acid. Therefore, detailed description for the method for producing the above expression plasmid is omitted here.

Thereafter, purified enzyme samples were produced by use of the produced expression plasmid, by a method identical to the method by which the purified enzyme samples shown in Table 3 were produced. The substrate specificity and the thermal stability of these purified enzyme samples were evaluated. The result of the evaluation is shown in Table 5.

TABLE 5

| I58X (–G110Q + F282Y) | F-V/F-VH | F-K/F-VH | Thermal stability (%) [ratio] |
|---|---|---|---|
| — | 4.0 | 0.06 | 44.6 [1.00] |
| T | 0.7 | 0.00 | 27.4 [0.61] |
| M | 1.4 | 0.05 | 84.5 [1.89] |
| S | 1.4 | 0.01 | 59.8 [1.34] |
| V | 1.6 | 0.01 | 44.0 [0.99] |
| A | 1.9 | 0.04 | 82.0 [1.84] |
| N | 2.6 | 0.00 | 6.6 [0.15] |
| L | 3.6 | 0.05 | 37.1 [0.83] |

As shown in Table 5, it is apparent that the mutant protein in which the isoleucine at 58$^{th}$ position of the amino acid sequence shown in SEQ ID NO: 1 has been also replaced with another amino acid in the pIE353-G110Q+F282Y also has smaller F-K/F-VH and F-V/F-VH than those of the unmodified fructosyl valyl histidine oxidase protein (IE353-F282Y), that is, the mutant protein has more improved substrate specificity than that of the unmodified fructosyl valyl histidine oxidase protein.

Further, as is clear from Table 5, the mutant protein in which the isoleucine is replaced with M, A or S has an improved thermal stability. It is accordingly apparent that a modified fructosyl valyl histidine oxidase in which mutation is further introduced into the amino acid sequence shown in SEQ ID NO: 1 acquires an improved substrate specificity by replacing the isoleucine at 58$^{th}$ position with another amino acid.

13. Reference Example 1

Fructosyl Valyl Histidine Oxidase Mutant Protein (Triple Mutant Protein) in which an Amino Acid is Yet Further Replaced with Another Amino Acid, and Property Evaluation of the Mutant Protein The above describes Example 10 in which the glycine at 110$^{th}$ position was replaced with glutamine. Meanwhile, the following describes whether or not an identical effect to that of Example 10 can be attained in a case where the glycine at 110$^{th}$ position is replaced with an amino acid other than glutamine. Specifically, the glycine at 110$^{th}$ position was replaced with an amino acid other than glutamine in an IE353-I58T+F282Y, and then the substrate specificity of the purified enzyme sample in which the glycine was replaced with the amino acid other than glutamine was examined.

First, an expression plasmid of a mutant protein in which the phenylalanine at 282$^{th}$ position of the amino acid sequence shown in SEQ ID NO: 1 was replaced with tyrosine and the isoleucine at 58$^{th}$ position of the amino acid sequence shown in SEQ ID NO: 1 was replaced with threonine was produced. The following described a method for producing the expression plasmid.

First, a primer R3 and a primer R4 were synthesized in order to randomly replace, with another amino acid, the glycine at 110th position of the amino acid sequence shown in SEQ ID NO: 1.

```
Primer R3:
                                          (SEQ ID NO: 11)
5'-snnagacttcaggtctgcaatgtcttttc-3'

Primer R4:
                                          (SEQ ID NO: 12)
5'-taccaagctctcgtggacgcgggcttggat-3'
```

Subsequently, a recombinant plasmid in which mutation was introduced into the glycine at 110$^{th}$ position was produced by use of the expression plasmid pIE353-I58T+G110Q+F282Y produced in Example 9, the primer R3, the primer R4 and the KOD-Plus Site-Directed Mutagenesis Kit.

Thereafter, the BL21 CodonPlus (DE3)-RIL was transformed by use of the recombinant plasmid, and then 100 colonies having an ampicillin resistance were selected. Subsequently, nucleotide sequences of 100 recombinant plasmids in the 100 colonies were examined. As a result of the examination, plasmids in which the glycine at 110$^{th}$ position of the amino acid sequence shown in SEQ ID NO: 1 was replaced with 19 types of amino acids (including a wild-type amino acid), respectively, were successfully acquired.

Specifically, a plasmid (pIE353-I58T+G110A+F282Y) in which a nucleotide sequence (gga) that encodes for 110$^{th}$ position of the amino acid sequence shown in SEQ ID NO: 1 was replaced with a nucleotide sequence (gcg) that encodes for alanine (A) was successfully acquired. A purified enzyme sample made from the plasmid is referred to as IE353-I58T+G110A+F282Y.

Further, a plasmid (pIE353-I58T+G110V+F282Y) in which the nucleotide sequence (gga) that encodes for 110$^{th}$ position of the amino acid sequence shown in SEQ ID NO: 1 was replaced with a nucleotide sequence (gtg) that encodes for valine (V) was successfully acquired. A purified enzyme sample made from the plasmid is referred to as IE353-I58T+G110V+F282Y.

Further, a plasmid (pIE353-I58T+G110L+F282Y) in which the nucleotide sequence (gga) that encodes for 110$^{th}$ position of the amino acid sequence shown in SEQ ID NO: 1 was replaced with a nucleotide sequence (ctg) that encodes for leucine (L) was successfully acquired. A purified enzyme sample made from the plasmid is referred to as IE353-I58T+G110L+F282Y.

Further, a plasmid (pIE353-I58T+G110M+F282Y) in which the nucleotide sequence (gga) that encodes for 110$^{th}$ position of the amino acid sequence shown in SEQ ID NO: 1 was replaced with a nucleotide sequence (atg) that encodes for methionine (M) was successfully acquired. A purified enzyme sample made from the plasmid is referred to as IE353-I58T+G110M+F282Y.

Further, a plasmid (pIE353-I58T+G110F+F282Y) in which the nucleotide sequence (gga) that encodes for 110$^{th}$ position of the amino acid sequence shown in SEQ ID NO: 1 was replaced with a nucleotide sequence (ttc) that encodes for phenylalanine (F) was successfully acquired. A purified enzyme sample made from the plasmid is referred to as IE353-I58T+G110F+F282Y.

Further, a plasmid (pIE353-I58T+G110S+F282Y) in which the nucleotide sequence (gga) that encodes for 110$^{th}$ position of the amino acid sequence shown in SEQ ID NO: 1 was replaced with a nucleotide sequence (tcc) that encodes for serine (S) was successfully acquired. A purified enzyme sample made from the plasmid is referred to as IE353-I58T+G110S+F282Y.

Further, a plasmid (pIE353-I58T+G110T+F282Y) in which the nucleotide sequence (gga) that encodes for 110$^{th}$ position of the amino acid sequence shown in SEQ ID NO: 1 was replaced with a nucleotide sequence (acg) that encodes for threonine (T) was successfully acquired. A purified enzyme sample made from the plasmid is referred to as IE353-I58T+G110T+F282Y.

Further, a plasmid (pIE353-I58T+G110C+F282Y) in which the nucleotide sequence (gga) that encodes for $110^{th}$ position of the amino acid sequence shown in SEQ ID NO: 1 was replaced with a nucleotide sequence (tgt) that encodes for cysteine (C) was successfully acquired. A purified enzyme sample made from the plasmid is referred to as IE353-I58T+G110C+F282Y.

Further, a plasmid (pIE353-I58T+G110Y+F282Y) in which the nucleotide sequence (gga) that encodes for $110^{th}$ position of the amino acid sequence shown in SEQ ID NO: 1 was replaced with a nucleotide sequence (tac) that encodes for tyrosine (Y) was successfully acquired. A purified enzyme sample made from the plasmid is referred to as IE353-I58T+G110Y+F282Y.

Further, a plasmid (pIE353-I58T+G110N+F282Y) in which the nucleotide sequence (gga) that encodes for $110^{th}$ position of the amino acid sequence shown in SEQ ID NO: 1 was replaced with a nucleotide sequence (aac) that encodes for asparagine (N) was successfully acquired. A purified enzyme sample made from the plasmid is referred to as IE353-I58T+G110N+F282Y.

Further, a plasmid (pIE353-I58T+G110K+F282Y) in which the nucleotide sequence (gga) that encodes for $110^{th}$ position of the amino acid sequence shown in SEQ ID NO: 1 was replaced with a nucleotide sequence (aag) that encodes for lycine (K) was successfully acquired. A purified enzyme sample made from the plasmid is referred to as IE353-I58T+G110K+F282Y.

Further, a plasmid (pIE353-I58T+G110H+F282Y) in which the nucleotide sequence (gga) that encodes for $110^{th}$ position of the amino acid sequence shown in SEQ ID NO: 1 was replaced with a nucleotide sequence (cac) that encodes for histidine (H) was successfully acquired. A purified enzyme sample made from the plasmid is referred to as IE353-I58T+G110H+F282Y.

Further, a plasmid (pIE353-I58T+G110R+F282Y) in which the nucleotide sequence (gga) that encodes for $110^{th}$ position of the amino acid sequence shown in SEQ ID NO: 1 was replaced with a nucleotide sequence (agg) that encodes for arginine (R) was successfully acquired. A purified enzyme sample made from the plasmid is referred to as IE353-I58T+G110R+F282Y.

Further, a plasmid (pIE353-I58T+G110D+F282Y) in which the nucleotide sequence (gga) that encodes for $110^{th}$ position of the amino acid sequence shown in SEQ ID NO: 1 was replaced with a nucleotide sequence (gac) that encodes for asparagine acid (D) was successfully acquired. A purified enzyme sample made from the plasmid is referred to as IE353-I58T+G110D+F282Y.

Further, a plasmid (pIE353-I58T+G110E+F282Y) in which the nucleotide sequence (gga) that encodes for $110^{th}$ position of the amino acid sequence shown in SEQ ID NO: 1 was replaced with a nucleotide sequence (gag) that encodes for glutamic acid (E) was successfully acquired. A purified enzyme sample made from the plasmid is referred to as IE353-I58T+G110E+F282Y.

Further, a plasmid (pIE353-I58T+G110W+F282Y) in which the nucleotide sequence (gga) that encodes for $110^{th}$ position of the amino acid sequence shown in SEQ ID NO: 1 was replaced with a nucleotide sequence (tgg) that encodes for tryptophan (W) was successfully acquired. A purified enzyme sample made from the plasmid is referred to as IE353-I58T+G110W+F282Y.

Further, a plasmid (pIE353-I58T+G110P+F282Y) in which the nucleotide sequence (gga) that encodes for $110^{th}$ position of the amino acid sequence shown in SEQ ID NO: 1 was replaced with a nucleotide sequence (ccc) that encodes for proline (P) was successfully acquired. A purified enzyme sample made from the plasmid is referred to as IE353-I58T+G110P+F282Y.

Further, a plasmid (pIE353-I58T+G110I+F282Y) in which the nucleotide sequence (gga) that encodes for $110^{th}$ position of the amino acid sequence shown in SEQ ID NO: 1 was replaced with a nucleotide sequence (att) that encodes for isoleucine (I) was successfully acquired. A purified enzyme sample made from the plasmid is referred to as IE353-I58T+G110I+F282Y.

Among the above purified enzyme samples, purified enzyme samples having a fructosyl valyl histidine oxidase activity were IE353-I58T+G110Q+F282Y, IE353-I58T+G110V+F282Y, IE353-I58T+G110L+F282Y, IE353-I58T+G110I+F282Y, IE353-I58T+G110M+F282Y, IE353-I58T+G110F+F282Y, IE353-I58T+G110S+F282Y, IE353-I58T+G110T+F282Y, IE353-I58T+G110Y+F282Y, IE353-I58T+G110N+F282Y, IE353-I58T+G110H+F282Y, IE353-I58T+G110R+F282Y, IE353-I58T+G110E+F282Y, IE353-I58T+G110K+F282Y, and IE353-I58T+G110D+F282Y. The substrate specificities of the purified enzyme samples having the fructosyl valyl histidine oxidase activity were evaluated. The result of the evaluation is shown in Table 6.

TABLE 6

| G110X (−I58T + F282Y) | F-V/F-VH |
|---|---|
| Q | 0.7 |
| V | 0.5 |
| L | 0.5 |
| I | 0.5 |
| M | 0.5 |
| F | 0.4 |
| S | 0.6 |
| T | 0.5 |
| Y | 0.4 |
| N | 0.6 |
| H | 0.4 |
| R | 0.6 |
| E | 0.4 |
| K | 0.4 |
| D | 0.5 |

As is clear from Table 6, the mutant protein in which the glycine at $110^{th}$ position of the amino acid sequence shown in SEQ ID NO: 1 is replaced with another amino acid in the IE353-I58T+F282Y also has smaller F-V/F-VH as with the IE353-I58T+G110Q+F282Y, that is, the mutant protein has an improved substrate specificity.

14. Activity Measurement Method

The following describes an activity measurement method of FAOD of Examples 8 through 10.

An enzyme activity of the FAOD to a substrate was calculated by measuring an increase in absorbance of a pigment as a result of peroxidase reaction involving hydrogen peroxide generated by enzyme reaction.

First, 3 ml of activity measuring reagent was heated at 37° C. for 5 minutes, and then 0.1 ml of enzyme solution diluted in advance by the enzyme diluent (the 50 mM potassium phosphate buffer (pH 6.5) including 0.1% of Triton X-100) was added to the activity measuring reagent, thereby starting the reaction.

The reaction was conducted at 37° C. for 5 minutes, and then a change in the absorbance at 500 nm per unit of time ($\Delta OD_{test}$/min) was measured. Meanwhile, a blank test was conducted by adding, instead of the enzyme solution, 0.1 ml of enzyme diluent to the activity measuring reagent, and then measuring a change in the absorbance at 500 nm ($\Delta OD_{blank}$/min), as with the above-described measurement.

An enzyme activity was calculated from the changes in the absorbance on the basis of the following formula, and is described by unit (U) where an amount of enzyme that oxidizes 1 micromole of substrate in one minute under the above-described condition is 1 unit (U). (Formula)

Activity value(U/ml)={(($\Delta$ODtest/min)−($\Delta$ODblank/min))×3.1(ml)×dilution magnification}/(13×1.0 (cm)×0.1(ml)).

In the above formula, "3.1 (ml)" is the whole liquid quantity, "13" is a millimolar absorbance index, "1.0 (cm)" is an optical length of a cell, and "0.1 (ml)" is the enzyme sample quantity.

15. Method for Calculating Specific Activity

A specific activity of Examples 8 through 10 was calculated from an activity value (U/mL) of a purified enzyme sample and an absorbance at 280 nm (A280) by the following formula.

(Formula)

Specific activity(U/A280)=activity value(U/mL)/A280 (Abs)

Note that it is considered that a greater specific activity value a purified enzyme sample has is more preferable.

16. Km Evaluation Method

The following describes a Km evaluation method of Examples 8 through 10.

An activity measuring reagent was prepared such that fructosyl valyl histidine serving as a substrate had a concentration of 1.75 mM or 0.35 mM.

The activity value of the purified enzyme sample was calculated by the activity measurement method with use of the activity measuring reagent.

(Formula)

Km evaluation=activity value(U/mL) in a case where a substrate has a concentration of 1.75 mM/activity value (U/mL) in a case where a substrate has a concentration of 0.35 mM.

The greater the Km evaluation value calculated by the formula is, the smaller the Km value (Michaelis constant) is (in other words, the more improved an affinity between a substrate and an enzyme is). Thus, a greater Km evaluation value is more preferable.

17. Substrate Specificity Evaluation Method

The following describes a substrate specificity evaluation method of FAOD of Examples 8 through 10.

First, an activity measuring reagent was prepared such that substrates (F-K: fructosyl lysine, F-V: fructosyl valine, and F-VH: fructosyl valyl histidine) each have a concentration of 2 mM. Subsequently, an activity value was calculated by the above-described activity measurement method. On the basis of the calculated activity value, an activity value ratio (substrate specificity) was calculated by the following formulas.

(F-V/F-VH)=(activity value in a case where F-V is a substrate)/(activity value in a case where F-VH is a substrate)

(F-K/F-VH)=(activity value in a case where F-K is a substrate)/(activity value in a case where F-VH is a substrate)

The smaller the activity value ratio calculated by the above formulas is, the more excellent specificity to F-VH a purified enzyme sample has. Thus, a smaller activity value ratio is more preferable.

18. Thermal Stability Evaluation Method

The following describes a thermal stability evaluation method of FAOD of Examples 8 through 10.

A purified enzyme sample was solved in the 50 mM potassium phosphate buffer (pH 6.5) to have a concentration of 0.1 mg/mL in the buffer, and then the 50 mM potassium phosphate buffer including the purified enzyme sample was heated at 50° C. for 10 minutes. In this manner, the thermal stability (%) of the purified enzyme sample was calculated by the following formula.

Thermal stability(%)={(activity value after heating at 50° C. for 10 minutes)/(activity value prior to heating)}×100

The greater the thermal stability value calculated by the above formula is, the more excellent thermal stability the purified enzyme sample has. Thus, a greater thermal stability value is more preferable.

19. Example 8

Modification of Fructosyl Valyl Histidine Oxidase Gene and Protein

First, a primer R3 and a primer R4 were synthesized in order to randomly replace, with another amino acid, the glycine at 110th position of the amino acid sequence shown in SEQ ID NO: 1.

```
Primer R3:
                                    (SEQ ID NO: 11)
5'-snnagacttcaggtctgcaatgtcttttttc-3'

Primer R4:
                                    (SEQ ID NO: 12)
5'-taccaagctctcgtggacgcgggcttggat-3'
```

Subsequently, a recombinant plasmid in which mutation was introduced into the glycine at $110^{th}$ position was produced by use of the pIE353, the primer R3, the primer R4 and the KOD-Plus Site-Directed Mutagenesis Kit (manufactured by TOYOBO Co., Ltd.). Thereafter, the BL21 CodonPlus (DE3)-RIL was transformed by use of the recombinant plasmid, and then 100 colonies having an ampicillin resistance were selected. Subsequently, nucleotide sequences of 100 recombinant plasmids in the 100 colonies were examined. As a result of the examination, plasmids in which the glycine at $110^{th}$ position of the amino acid sequence shown in SEQ ID NO: 1 was replaced with 19 types of amino acids (except a wild-type glycine), respectively, were successfully acquired.

Specifically, a plasmid (pIE353-G110T) in which a nucleotide sequence (gga) that encodes for the glycine at $110^{th}$ position of the amino acid sequence shown in SEQ ID NO: 1 was replaced with a nucleotide sequence (acg) that encodes for threonine (T) was successfully acquired. A purified enzyme sample made from the plasmid is referred to as IE353-G110T.

Further, a plasmid (pIE353-G110A) in which the nucleotide sequence (gga) that encodes for the glycine at $110^{th}$ position of the amino acid sequence shown in SEQ ID NO: 1 was replaced with a nucleotide sequence (gcg) that encodes for alanine (A) was successfully acquired. A purified enzyme sample made from the plasmid is referred to as IE353-G110A.

Further, a plasmid (pIE353-G110V) in which the nucleotide sequence (gga) that encodes for the glycine at $110^{th}$ position of the amino acid sequence shown in SEQ ID NO: 1 was replaced with a nucleotide sequence (gtg) that encodes for valine (V) was successfully acquired. A purified enzyme sample made from the plasmid is referred to as IE353-G110V.

Further, a plasmid (pIE353-G110L) in which the nucleotide sequence (gga) that encodes for the glycine at $110^{th}$ position of the amino acid sequence shown in SEQ ID NO: 1 was replaced with a nucleotide sequence (ctg) that encodes for leucine (L) was successfully acquired. A purified enzyme sample made from the plasmid is referred to as IE353-G110L.

Further, a plasmid (pIE353-G110I) in which the nucleotide sequence (gga) that encodes for the glycine at $110^{th}$ position of the amino acid sequence shown in SEQ ID NO: 1 was replaced with a nucleotide sequence (att) that encodes for isoleucine (I) was successfully acquired. A purified enzyme sample made from the plasmid is referred to as IE353-G110I.

Further, a plasmid (pIE353-G110M) in which the nucleotide sequence (gga) that encodes for the glycine at $110^{th}$ position of the amino acid sequence shown in SEQ ID NO: 1 was replaced with a nucleotide sequence (atg) that encodes for methionine (M) was successfully acquired. A purified enzyme sample made from the plasmid is referred to as IE353-G110M.

Further, a plasmid (pIE353-G110F) in which the nucleotide sequence (gga) that encodes for the glycine at $110^{th}$ position of the amino acid sequence shown in SEQ ID NO: 1 was replaced with a nucleotide sequence (ttc) that encodes for phenylalanine (F) was successfully acquired. A purified enzyme sample made from the plasmid is referred to as IE353-G110F.

Further, a plasmid (pIE353-G110S) in which the nucleotide sequence (gga) that encodes for the glycine at $110^{th}$ position of the amino acid sequence shown in SEQ ID NO: 1 was replaced with a nucleotide sequence (tcc) that encodes for serine (S) was successfully acquired. A purified enzyme sample made from the plasmid is referred to as IE353-G110S.

Further, a plasmid (pIE353-G110Q) in which the nucleotide sequence (gga) that encodes for the glycine at $110^{th}$ position of the amino acid sequence shown in SEQ ID NO: 1 was replaced with a nucleotide sequence (cag) that encodes for glutamine (Q) was successfully acquired. A purified enzyme sample made from the plasmid is referred to as IE353-G110Q.

Further, a plasmid (pIE353-G110C) in which the nucleotide sequence (gga) that encodes for the glycine at $110^{th}$ position of the amino acid sequence shown in SEQ ID NO: 1 was replaced with a nucleotide sequence (tgt) that encodes for cysteine (C) was successfully acquired. A purified enzyme sample made from the plasmid is referred to as IE353-G110C.

Further, a plasmid (pIE353-G110Y) in which the nucleotide sequence (gga) that encodes for the glycine at $110^{th}$ position of the amino acid sequence shown in SEQ ID NO: 1 was replaced with a nucleotide sequence (tac) that encodes for tyrosine (Y) was successfully acquired. A purified enzyme sample made from the plasmid is referred to as IE353-G110Y.

Further, a plasmid (pIE353-G110N) in which the nucleotide sequence (gga) that encodes for the glycine at $110^{th}$ position of the amino acid sequence shown in SEQ ID NO: 1 was replaced with a nucleotide sequence (aac) that encodes for asparagine (N) was successfully acquired. A purified enzyme sample made from the plasmid is referred to as IE353-G110N.

Further, a plasmid (pIE353-G110K) in which the nucleotide sequence (gga) that encodes for the glycine at $110^{th}$ position of the amino acid sequence shown in SEQ ID NO: 1 was replaced with a nucleotide sequence (aag) that encodes for lysine (K) was successfully acquired. A purified enzyme sample made from the plasmid is referred to as IE353-G110K.

Further, a plasmid (pIE353-G110H) in which the nucleotide sequence (gga) that encodes for the glycine at $110^{th}$ position of the amino acid sequence shown in SEQ ID NO: 1 was replaced with a nucleotide sequence (cac) that encodes for histidine (H) was successfully acquired. A purified enzyme sample made from the plasmid is referred to as IE353-G110H.

Further, a plasmid (pIE353-G110R) in which the nucleotide sequence (gga) that encodes for the glycine at $110^{th}$ position of the amino acid sequence shown in SEQ ID NO: 1 was replaced with a nucleotide sequence (agg) that encodes for arginine (R) was successfully acquired. A purified enzyme sample made from the plasmid is referred to as IE353-G110R.

Further, a plasmid (pIE353-G110D) in which the nucleotide sequence (gga) that encodes for the glycine at $110^{th}$ position of the amino acid sequence shown in SEQ ID NO: 1 was replaced with a nucleotide sequence (gac) that encodes for asparagine acid (D) was successfully acquired. A purified enzyme sample made from the plasmid is referred to as IE353-G110D.

Further, a plasmid (pIE353-G110E) in which the nucleotide sequence (gga) that encodes for the glycine at $110^{th}$ position of the amino acid sequence shown in SEQ ID NO: 1 was replaced with a nucleotide sequence (gag) that encodes for glutamic acid (E) was successfully acquired. A purified enzyme sample made from the plasmid is referred to as IE353-G110E.

Further, a plasmid (pIE353-G110W) in which the nucleotide sequence (gga) that encodes for the glycine at $110^{th}$ position of the amino acid sequence shown in SEQ ID NO: 1 was replaced with a nucleotide sequence (tgg) that encodes for tryptophan (W) was successfully acquired. A purified enzyme sample made from the plasmid is referred to as IE353-G110W.

Further, a plasmid (pIE353-G110P) in which the nucleotide sequence (gga) that encodes for the glycine at $110^{th}$ position of the amino acid sequence shown in SEQ ID NO: 1 was replaced with a nucleotide sequence (ccc) that encodes for proline (P) was successfully acquired. A purified enzyme sample made from the plasmid is referred to as IE353-G110P.

Subsequently, the BL21 CodonPlus (DE3)-RIL was transformed by use of the respective acquired plasmids, and then a transformant having an ampicillin resistance was selected.

As is the case with the above-described IE353, the selected transformant was cultured, and then a crude enzyme solution acquired by culturing the selected transformant was purified. As a result, purified enzyme samples (IE353-G110Q, IE353-G110A, IE353-G110V, IE353-G110L, IE353-G110I, IE353-G110M, IE353-G110F, IE353-G110S, IE353-G110T, IE353-G110C, IE353-G110Y, IE353-G110N, IE353-

G110K, IE353-G110H, IE353-G110R, IE353-G110D, IE353-G110E, IE353-G110W, and IE353-G110P) were acquired.

The above purified enzyme samples were analyzed by SDS-polyacrylamide gel electrophoresis. As a result of the analysis, it was confirmed that the purified enzyme samples each comprised a single protein.

20. Example 9

Property Evaluation of Fructosyl Valyl Histidine Oxidase Mutant Protein

First, enzyme activities of a wild-type fructosyl valyl histidine oxidase (IE353) and the 19 types of purified enzyme samples (IE353-G110Q, IE353-G110A, IE353-G110V, IE353-G110L, IE353-G110I, IE353-G110M, IE353-G110F, IE353-G110S, IE353-G110T, IE353-G110C, IE353-G110Y, IE353-G110N, IE353-G110K, IE353-G110H, IE353-G110R, IE353-G110D, IE353-G110E, IE353-G110W, and IE353-G110P) were measured by the above-described activity measurement method (with use of fructosyl valyl histidine as a substrate).

The fructosyl valyl histidine activity was not detected from the IE353-G110P. Therefore, the purified enzyme samples other than the IE353-G110P were evaluated on their thermal stability, specific activity, Km value and substrate specificity. The result of the evaluation is shown in Table 7. Note that "amino acid X" in Table 7 indicates an amino acid with which the glycine at $110^{th}$ position is replaced (in other words, X of IE353-G110X).

TABLE 7

| Amino acid X | Thermal stability (%) [ratio] | Specific activity | Km evaluation | F-K/F-VH | F-V/F-VH |
|---|---|---|---|---|---|
| — | 56.1 [1.00] | 2.3 | 0.71 | 0.10 | 5.0 |
| Q | 80.7 [1.44] | 3.3 | 0.70 | 0.10 | 4.8 |
| M | 79.9 [1.42] | 3.2 | 0.71 | 0.18 | 3.7 |
| E | 79.0 [1.41] | 5.8 | 0.62 | 0.03 | 2.4 |
| T | 78.3 [1.40] | 3.1 | 0.69 | 0.12 | 4.6 |
| A | 76.2 [1.36] | 4.4 | 0.61 | 0.11 | 3.4 |
| C | 74.5 [1.33] | 3.3 | 0.55 | 0.14 | 3.4 |
| H | 74.3 [1.32] | 3.3 | 0.82 | 0.33 | 5.8 |
| K | 72.8 [1.30] | 2.9 | 0.70 | 0.21 | 5.6 |
| N | 72.5 [1.29] | 3.7 | 0.72 | 0.11 | 4.5 |
| R | 72.0 [1.28] | 2.7 | 0.68 | 0.21 | 5.2 |
| S | 69.4 [1.24] | 2.9 | 0.68 | 0.09 | 4.1 |
| V | 65.2 [1.16] | 4.3 | 0.71 | 0.16 | 4.2 |
| L | 64.5 [1.15] | 3.4 | 0.74 | 0.15 | 4.7 |
| D | 64.2 [1.14] | 3.8 | 0.67 | 0.04 | 3.3 |
| I | 62.3 [1.11] | 3.5 | 0.73 | 0.26 | 4.5 |
| Y | 62.2 [1.11] | 5.0 | 0.78 | 0.24 | 3.4 |
| F | 58.2 [1.04] | 3.6 | 0.76 | 0.35 | 4.4 |
| W | 32.4 [0.58] | 2.6 | 0.73 | 0.18 | 2.6 |
| P | — | — | — | — | — |

As is clear from Table 7, mutants other than the IE353-G110W, in each of which mutants the glycine at $110^{th}$ position of the amino acid sequence shown in SEQ ID NO: 1 is replaced with another amino acid each have more improved thermal stability than that of the wild-type fructosyl valyl histidine oxidase (IE353).

Further, as shown in Table 7, it is apparent that the purified enzyme samples each include a modified protein having preferable specific activity, Km evaluation, and substrate specificity (F-K/F-VH, F-V/F-VH). For example, a purified enzyme sample in which the glycine at $110^{th}$ position is replaced with glutamic acid (E) has substantially 2.5 times of specific activity as great as that of the wild-type fructosyl valyl histidine oxidase (IE353), and also has more improved substrate specificity than that of the wild-type fructosyl valyl histidine oxidase (IE353). It is therefore apparent that replacement of the glycine at $110^{th}$ position with another amino acid causes not only thermal stability but also other properties to be improved.

21. Example 10

Fructosyl Valyl Histidine Oxidase Mutant Protein (Double Mutant Protein) in which an Amino Acid is Further Replaced with Another Amino Acid, and Property Evaluation of the Mutant Protein The following describes how a property of a mutant protein changed in a case where in the mutant protein, an amino acid other than the glycine at $110^{th}$ position of the amino acid sequence shown in SEQ ID NO: 1 was also replaced with another amino acid in addition to replacement of the glycine.

First, an expression plasmid of a mutant protein in which the phenylalanine at $282^{th}$ position of the amino acid sequence shown in SEQ ID NO: 1 was replaced with tyrosine was produced. The following describes a method for producing the expression plasmid.

First, a primer Y1 and a primer Y2 were synthesized in order to replace, with tyrosine, the phenylalanine at $282^{th}$ position of the amino acid sequence shown in SEQ ID NO: 1.

```
Primer Y1:
                                (SEQ ID NO: 7)
5'-tatacgcgcttcaagatgcatcaacccttttggcg-3'

Primer Y2:
                                (SEQ ID NO: 8)
5'-gccaggaaactcgtcgcagactttgatcacg-3'
```

Thereafter, a recombinant plasmid in which the phenylalanine at $282^{th}$ position was replaced with tyrosine was produced by use of the pIE353, the primer Y1, the primer Y2 and the KOD-Plus Site-Directed Mutagenesis Kit (manufactured by TOYOBO Co., Ltd.). Specifically, the recombinant plasmid (pIE353-F282Y) in which a nucleotide sequence (ttc) that encodes for the phenylalanine at $282^{th}$ position of the amino acid sequence shown in SEQ ID NO: 1 was replaced with a nucleotide sequence (tat) that encodes for tyrosine (Y) was successfully acquired.

From the acquired recombinant plasmid (pIE353-F282Y), a desired purified enzyme sample (IE353-F282Y) was produced by a method identical to the method for producing the above-described purified enzyme samples.

As shown in Table 8, the purified enzyme sample (IE353-F282Y) made from the pIE353-F282Y has more improved thermal stability than that of the wild-type fructosyl valyl histidine oxidase (IE353).

TABLE 8

|  | Thermal stability (%) [ratio] |
|---|---|
| IE353 | 75.2 [1.00] |
| IE353 – F282Y | 92.1 [1.22] |

Subsequently, an expression plasmid of a mutant protein in which the glycine at $110^{th}$ position was also replaced with another amino acid in addition to replacing the phenylalanine at $282^{th}$ position with tyrosine was produced by use of the pIE353-F282Y, the primer R3, the primer R4 and the KOD-Plus Site-Directed Mutagenesis Kit (manufactured by TOYOBO Co., Ltd.). A method for producing the above expression plasmid is basically identical to that for producing the expression plasmid of the mutant protein in which only the glycine at $110^{th}$ position is replaced with another amino acid. Therefore, detailed description for the method for producing the above expression plasmid is omitted here.

Thereafter, purified enzyme samples were produced by use of the produced expression plasmid, by a method identical to the method for producing the purified enzyme samples shown in Table 7. Properties of these purified enzyme samples were evaluated. However, the fructosyl valyl histidine oxidase activity was not detected from the IE353-G110P+F282Y. Therefore, the purified enzyme samples other than the IE353-G110P+F282Y were evaluated on their properties. The result of the evaluation is shown in Table 9. Note that "amino acid X" in Table 9 indicates an amino acid with which the glycine at $110^{th}$ position is replaced (in other words, X of IE353-G110X+F282Y).

TABLE 9

| Amino acid X | Thermal stability (%) [ratio] | Specific activity | Km evaluation | F-K/F-VH | F-V/F-VH |
|---|---|---|---|---|---|
| — | 87.2 [1.00] | 3.3 | 0.71 | 0.08 | 3.8 |
| Q | 98.5 [1.13] | 4.2 | 0.67 | 0.07 | 3.5 |
| A | 97.8 [1.12] | 4.4 | 0.61 | 0.11 | 3.4 |
| E | 96.7 [1.11] | 5.2 | 0.55 | 0.06 | 2.6 |
| N | 95.9 [1.10] | 5.5 | 0.54 | 0.05 | 2.4 |
| H | 95.8 [1.10] | 2.9 | 0.79 | 0.23 | 5.0 |
| T | 94.8 [1.09] | 3.6 | 0.66 | 0.08 | 3.6 |
| K | 93.2 [1.07] | 3.3 | 0.68 | 0.17 | 4.6 |
| D | 93.0 [1.07] | 4.6 | 0.60 | 0.02 | 2.5 |

TABLE 9-continued

| Amino acid X | Thermal stability (%) [ratio] | Specific activity | Km evaluation | F-K/F-VH | F-V/F-VH |
|---|---|---|---|---|---|
| M | 92.8 [1.06] | 3.2 | 0.71 | 0.15 | 3.4 |
| R | 92.4 [1.06] | 3.6 | 0.67 | 0.16 | 4.3 |
| L | 91.5 [1.05] | 3.5 | 0.72 | 0.17 | 3.7 |
| V | 91.3 [1.05] | 4.4 | 0.69 | 0.12 | 3.3 |
| S | 90.5 [1.04] | 3.5 | 0.71 | 0.06 | 3.6 |
| Y | 89.7 [1.03] | 4.6 | 0.76 | 0.17 | 2.7 |
| I | 88.2 [1.01] | 2.9 | 0.67 | 0.17 | 3.3 |
| F | 88.1 [1.01] | 3.4 | 0.72 | 0.27 | 3.4 |
| C | 88.0 [1.01] | 3.7 | 0.56 | 0.11 | 2.7 |
| W | 78.0 [0.89] | 5.3 | 0.65 | 0.17 | 2.1 |
| P | — | — | — | — | — |

As is clear from Table 9, the IE353-F282Y in which the glycine at $110^{th}$ position is also replaced with another amino acid still has an improved thermal stability.

Further, some of the purified enzyme samples have preferable specific activity, Km evaluation and substrate specificity (F-K/F-VH, F-V/F-VH).

As a result, it is apparent that it is possible to improve the thermal stability by further replacing the glycine at $110^{th}$ position with another amino acid in addition to introduction of mutation into an amino acid other than the glycine at $110^{th}$ position of the amino acid sequence shown in SEQ ID NO: 1.

The present invention is not limited to the description of the embodiments and examples above, but may be altered by a skilled person within the scope of the claims. An embodiment and an example based on a proper combination of technical means disclosed in different embodiments and examples are encompassed in the technical scope of the present invention. Further, all documents described in the present specification are used as a reference.

Industrial Applicability

According to the present invention, it is possible to create and provide a novel protein having a fructosyl histidine oxidase activity which protein is useful for measurement of fructosyl valyl histidine. Further, the present invention provides: a method for measuring fructosyl valyl histidine or the like with use of the protein; a reagent composition for measuring fructosyl valyl histidine or the like; and the like. This can contribute to further progress of clinical examination in accordance with preventive medicine.

Further, the present invention provides a fructosyl valyl histidine oxidase which is useful for measurement of fructosyl valyl histidine and which has excellent substrate specificity and/or thermal stability. It is therefore possible to provide: a method for measuring, with high accuracy, fructosyl valyl histidine with use of the fructosyl valyl histidine oxidase; a reagent composition for measuring fructosyl valyl histidine; and the like. Accordingly, the present invention is applicable to industries related to the field of clinical examination in accordance with the preventive medicine, the field of diagnostic medical care, the field of medicine manufacture, the field of health medical science, and the filed of life science.

The invention claimed is:

1. A protein having a fructosyl valyl histidine oxidase activity, the protein being any one of proteins (I) through (III), below:

(I) a protein comprising the amino acid sequence shown in SEQ ID NO: 1;

(II) a protein comprising the amino acid sequence shown in SEQ ID NO: 1 in which 10 or less amino acid residues are replaced, deleted, inserted and/or added, the protein having the fructosyl valyl histidine oxidase activity; and (III) a protein comprising an amino acid sequence having 90% or greater homology with the amino acid sequence shown in SEQ ID NO: 1, the protein having the fructosyl valyl histidine oxidase activity, wherein, in the proteins of (II) and (III), glycine at 110th position from the amino terminal is replaced with an amino acid selected from the group consisting of methionine, threonine, cysteine, histidine, asparagine, arginine, serine, valine, leucine, asparagine acid, isoleucine, tyrosine, phenylalanine, glutamine, lysine, glutamic acid and alanine.

2. The protein as set forth in claim 1, wherein: the protein is the protein described in (II) or (III), and isoleucine at 58th position from the amino terminal is replaced with another amino acid.

3. The protein as set forth in claim 1, wherein: the protein is the protein described in (II) or (III), and phenylalanine at 282th position from the amino terminal is replaced with another amino acid.

4. The protein as set forth in claim 2, wherein: the isoleucine at 58th position from the amino terminal is replaced with methionine, threonine, alanine, asparagine, serine, valine or leucine.

5. The protein as set forth in claim 3, wherein: the phenylalanine at 282th position from the amino terminal is replaced with tyrosine.

6. A method for measuring a glycosylated protein, comprising the step of causing a protein as set forth in claim 1 to act on a glycosylated amine.

7. A method for measuring glycosylated hemoglobin included in a sample, comprising the steps of:
preparing a glycosylated amine by use of the glycosylated hemoglobin included in the sample; and
causing a protein as set forth in claim 1 to act on the sample.

* * * * *

SEQUENCE LISTING

<160> NUMBER OF SEQ ID NOS: 12

<210> SEQ ID NO 1
<211> LENGTH: 437
<212> TYPE: PRT
<213> ORGANISM: Phaeosphaeria nodorum

<400> SEQUENCE: 1

Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
                20                  25                  30

Thr Pro Ser Asn Val Thr Val Leu Asp Ala Tyr Pro Ile Pro Ser Ser
                35                  40                  45

Gln Ser Ala Gly Asn Asp Leu Asn Lys Ile Met Gly Val Ser Leu Arg
    50                  55                  60

Asn Pro Val Asp Leu Gln Leu Ala Leu Glu Ala Arg Gln Met Trp Asn
65                  70                  75                  80

Glu Asp Glu Leu Phe Lys Lys Phe His Asn Thr Gly Arg Leu Asp
                85                  90                  95

Cys Ala His Gly Glu Lys Asp Ile Ala Asp Leu Lys Ser Gly Tyr Gln
                100                 105                 110

Ala Leu Val Asp Ala Gly Leu Asp Ala Thr Asn Glu Trp Leu Asp Ser
                115                 120                 125

Glu Asp Glu Ile Leu Lys Arg Met Pro Leu Leu Ser Arg Asp Gln Ile
    130                 135                 140

Lys Gly Trp Lys Ala Ile Phe Ser Lys Asp Gly Gly Trp Leu Ala Ala
145                 150                 155                 160

Ala Lys Ala Ile Asn Ala Val Gly Glu Tyr Leu Arg Asp Gln Gly Val
                165                 170                 175

Arg Phe Gly Phe Tyr Gly Ala Gly Ser Phe Lys Ala Pro Leu Leu Ala
                180                 185                 190

Glu Gly Val Cys Ile Gly Val Glu Thr Val Asp Gly Thr Arg Tyr Tyr
                195                 200                 205

Ala Asp Lys Val Val Leu Ala Ala Gly Ala Trp Ser Pro Thr Leu Val
    210                 215                 220

Glu Leu His Glu Gln Cys Val Ser Lys Ala Trp Val Tyr Gly His Ile
225                 230                 235                 240

Gln Leu Thr Pro Glu Glu Ala Ala Arg Tyr Lys Asn Ser Pro Val Val
                245                 250                 255

Tyr Asn Gly Asp Val Gly Phe Phe Glu Pro Asn Glu His Gly Val
                260                 265                 270

Ile Lys Val Cys Asp Glu Phe Pro Gly Phe Thr Arg Phe Lys Met His
                275                 280                 285

Gln Pro Phe Gly Ala Lys Ala Pro Lys Arg Ile Ser Val Pro Arg Ser
    290                 295                 300

His Ala Lys His Pro Thr Asp Thr Ile Pro Asp Ala Ser Asp Val Ser
305                 310                 315                 320

Ile Arg Arg Ala Ile Ala Thr Phe Met Pro Gln Phe Lys Asn Lys Lys
                325                 330                 335

Met Phe Asn Gln Ala Met Cys Trp Cys Thr Asp Thr Ala Asp Ala Ala
                340                 345                 350

Leu Leu Ile Cys Glu His Pro Glu Trp Lys Asn Phe Val Leu Ala Thr
                355                 360                 365

```
Gly Asp Ser Gly His Ser Phe Lys Leu Leu Pro Asn Ile Gly Lys His
    370             375                 380

Val Val Glu Leu Leu Glu Gly Thr Leu Ala Asp Asp Leu Ala His Ala
385             390                 395                 400

Trp Arg Trp Arg Pro Gly Ser Gly Asp Ala Leu Lys Ser Arg Arg Ser
                405                 410                 415

Ala Pro Ala Lys Asp Leu Ala Asp Met Pro Gly Trp Asn His Asp Lys
            420                 425                 430

Pro Arg Ala Asn Leu
        435

<210> SEQ ID NO 2
<211> LENGTH: 1314
<212> TYPE: DNA
<213> ORGANISM: Phaeosphaeria nodorum

<400> SEQUENCE: 2
atggcgccct ccagagcaaa caccagtgtc attgttgttg gtggtggagg gaccattggg      60
tcgtctactg ctcttcatct tgtgcgctca ggctatacac catcgaatgt acagtgctc     120 gatgcatacc caattccttc atcgcaatct gcaggcaatg acctcaataa gattatgggc    180
gttagcttgc gaaacccagt ggacctgcag ctggctctcg aggcgaggca gatgtggaac    240
gaagatgagc tgttcaagaa gttcttccac aacactggaa ggctcgactg tgcgcatggc    300
gaaaaagaca ttgcagacct gaagtctgga taccaagctc tcgtggacgc gggcttggat    360
gctacaaacg aatggctaga ctccgaggac gagatcctta agcgaatgcc acttcttttcc   420 cgtgaccaga tcaaaggctg gaaagcgatc ttcagtaaag atggcggctg gctcgcagca    480
gcgaaagcca tcaacgccgt cggcgagtat ctgcgggacc aaggtgtaag attcggattc    540
tatggcgcgg gctcgttcaa agcacctctg cttgctgaag gcgtgtgtat tggtgttgag    600
actgttgatg aacaaggta ctatgccgac aaagtcgttc ttgcagcagg agcatggagt     660
cccacacttg ttgaactgca tgagcaatgt gtttcgaagg cctgggtata tggccacata    720
caattgactc cagaagaggc cgctcgatac aagaacagcc ctgttgtata caacggtgac    780
gttggctttt tcttcgagcc caacgagcac ggcgtgatca aagtctgcga cgagtttcct    840
ggcttcacgc gcttcaagat gcatcaaccc tttggcgcaa aagcaccgaa gcgtatttca    900
gtaccaagat cgcatgctaa gcaccccacc gacacgatac tgatgcttc cgatgtgagt     960 atcaggaggg cgattgcgac tttcatgccg cagttcaaaa acaagaaaat gttcaaccag   1020
gcaatgtgtt ggtgcacaga tacagcggat gcagctttgc tgatctgtga acatccggaa   1080
tggaagaact ttgtacttgc aactggtgat agtgggcact cgttcaagct tctgccaaat   1140
attggcaagc atgttgttga actgctcgaa gggacacttg cagatgactt ggcgcacgcc   1200
tggagatggc ggcctgggtc tggtgatgcg ctcaagtcgc gcagatcagc gcctgcaaag   1260
gaccttgcgg acatgcctgg ttggaatcat gataagccga gggcgaactt gtag         1314

<210> SEQ ID NO 3
<211> LENGTH: 43
<212> TYPE: DNA
<213> ORGANISM: Artificial Sequence
<220> FEATURE:
<223> OTHER INFORMATION: Description of Artificial Sequence:artificially
      synthesized primer sequence

<400> SEQUENCE: 3
ggaattccat atggcgccct ccagagcaaa caccagtgtc att                       43
```

```
<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence:artificially
      synthesized primer sequence

<400> SEQUENCE: 4
ccgctcgagc aagttcgccc tcggcttatc atgattccaa cc                          42

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence:artificially
      synthesized primer sequence

<400> SEQUENCE: 5
cttattgagg tcattgcctg cagattgcga tgaagg                                 36

<210> SEQ ID NO 6
<211> LENGTH: 33
<212> TYPE: DNA
<213> ORGANISM: Artificial Sequence
<220> FEATURE:
<221> NAME/KEY: misc_feature
<222> LOCATION: (1),(2)
<223> OTHER INFORMATION: n stands for any base
<220> FEATURE:
<221> NAME/KEY: misc_feature
<222> LOCATION: (3)
<223> OTHER INFORMATION: s stands for guanine or cytosine

<400> SEQUENCE: 6
nnsatgggcg ttagcttgcg aaacccagtg gac                                    33

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence:artificially
      synthesized primer sequence

<400> SEQUENCE: 7
tatacgcgct tcaagatgca tcaacccttt ggcg                                   34

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence:artificially
      synthesized primer sequence

<400> SEQUENCE: 8
gccaggaaac tcgtcgcaga ctttgatcac g                                      31

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:artificially
      synthesized primer sequence
```

```
<400> SEQUENCE: 9
taccaagctc tcgtggacgc gggcttggat                                    30

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence:artificially
      synthesized primer sequence

<400> SEQUENCE: 10
cagtaccaag ctctcgtgga cgcgggctt                                     29

<210> SEQ ID NO 11
<211> LENGTH: 30
<212> TYPE: DNA
<213> ORGANISM: Artificial Sequence
<220> FEATURE:
<221> NAME/KEY: misc_feature
<222> LOCATION: (1)
<223> OTHER INFORMATION: s stands for guanine or cytosine
<220> FEATURE:
<221> NAME/KEY: misc_feature
<222> LOCATION: (2),(3)
<223> OTHER INFORMATION: n stands for any base
<220> FEATURE:
<223> OTHER INFORMATION: Description of Artificial Sequence:artificially
      synthesized primer sequence

<400> SEQUENCE: 11
snnagacttc aggtctgcaa tgtcttttc                                     30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:artificially
      synthesized primer sequence

<400> SEQUENCE: 12
taccaagctc tcgtggacgc gggcttggat                                    30
```